US011697632B2

(12) United States Patent
Edgar et al.

(10) Patent No.: US 11,697,632 B2
(45) Date of Patent: *Jul. 11, 2023

(54) STORAGE STABLE CHOLINE CHLORIDE COMPOSITIONS

(71) Applicant: Balchem Corporation, New Hampton, NY (US)

(72) Inventors: Jerry Edgar, New Hampton, NY (US); Michael Ibrahim, New Hampton, NY (US)

(73) Assignee: Balchem Corporation, New Hampton, NY (US)

( * ) Notice: Subject to any disclaimer, the term of this patent is extended or adjusted under 35 U.S.C. 154(b) by 86 days.

This patent is subject to a terminal disclaimer.

(21) Appl. No.: 17/500,658

(22) Filed: Oct. 13, 2021

(65) Prior Publication Data

US 2022/0064103 A1    Mar. 3, 2022

Related U.S. Application Data

(63) Continuation of application No. 16/749,636, filed on Jan. 22, 2020, now Pat. No. 11,180,442.

(60) Provisional application No. 62/798,855, filed on Jan. 30, 2019.

(51) Int. Cl.
| C07C 215/40 | (2006.01) |
| B02C 4/42 | (2006.01) |
| B30B 15/00 | (2006.01) |
| B30B 3/00 | (2006.01) |
| B02C 4/02 | (2006.01) |

(52) U.S. Cl.
CPC .............. *C07C 215/40* (2013.01); *B02C 4/02* (2013.01); *B02C 4/42* (2013.01); *B30B 3/005* (2013.01); *B30B 15/0005* (2013.01)

(58) Field of Classification Search
None
See application file for complete search history.

(56) References Cited

U.S. PATENT DOCUMENTS

| 3,356,569 | A | 12/1967 | Nicodemus et al. |
| 4,820,532 | A | 4/1989 | Bayer et al. |
| 5,906,843 | A | 5/1999 | Dew et al. |
| 7,923,033 | B2 | 4/2011 | Cavassini et al. |
| 2009/0123550 | A1 | 5/2009 | Phillips et al. |
| 2009/0202634 | A1 | 8/2009 | Jans et al. |
| 2012/0045550 | A1 | 2/2012 | Stokkers et al. |
| 2018/0092379 | A1 | 4/2018 | Becker et al. |

FOREIGN PATENT DOCUMENTS

CN        102450257 A    5/2012

OTHER PUBLICATIONS

Extended European Search Report in EP Application No. 20747999.9 dated Sep. 29, 2022; 6 pages.
Browning, J.E. "Agglomeration: Growing Larger in Applications and Technology," Chemical Engineering, Access Intelligence Association, Dec. 4, 1967, pp. 147-170.
International Search Report and Written Opinion for PCT/US2020/014550 dated Apr. 6, 2020, 10 pages.

*Primary Examiner* — Sudhakar Katakam
*Assistant Examiner* — Jennifer C Sawyer
(74) *Attorney, Agent, or Firm* — Polsinelli PC

(57) ABSTRACT

The present disclosure encompasses a composition comprising three-dimensional shapes, wherein each shape consists essentially of choline chloride, and methods of making such three-dimensional shapes.

19 Claims, 13 Drawing Sheets

STORAGE STABLE CHOLINE CHLORIDE COMPOSITIONS

CROSS REFERENCE TO RELATED APPLICATIONS

This application is a continuation of U.S. application Ser. No. 16/749,636 filed Jan. 22, 2020, which claims priority to U.S. Provisional Application No. 62/798,855, filed Jan. 30, 2019, the disclosures of which are incorporated herein by reference in their entirety.

FIELD

The present disclosure encompasses a composition comprising three-dimensional shapes, wherein each shape consists essentially of choline chloride, and methods of making such three-dimensional shapes.

BACKGROUND

An important characteristic of powders and granular material is flowability—i.e., the ease with which a powder or a granular material will flow under a specified set of conditions. Many powders and granular materials tend to undergo an aggregation process known as caking. Caking may be manifested as severe formation of hard lumps or even complete solidification into a rock hard mass. Caking adversely affects manufacturing processes, resulting in increased wear and tear on machines and possibly complete blockage of storage equipment or dosing units.

While exposure to high temperatures and/or humidity promotes caking for most powders and granular materials, for commercial choline chloride crystals (e.g., choline chloride as specified by the United States Pharmacopoeia) caking problems occur even in closed, temperature-controlled packing. Because of the extreme hygroscopic nature of choline chloride, choline chloride particles readily cake and bridge together to form a solid mass in packaging, making the final product difficult or impossible to handle. Hydrophobic, surface active compounds as well as cocrystallization have been used successfully in trials to overcome caking problems during crystallization and afterwards, but solutions either require the presence of these compounds in the final product or are difficult to remove from the final product.

Accordingly, there remains a need in the art for choline chloride compositions that have improved handling, and methods of preparing the same.

SUMMARY

Among the various aspects of the present disclosure encompasses a composition comprising three-dimensional shapes, wherein each shape consists essentially of choline chloride, and no dimension of each shape may measure more than 40 mm or less than 5 mm. In some embodiments, the composition comprises no more than 0.5% water immediately after production, as determined by Method I <921> USP 38 and/or the composition comprises no more than 0.5% water after one year of storage in moisture resistant packaging, as determined by Method I <921> USP 38. Alternatively or in addition, in some embodiments the composition does not substantially cake after storage of at least one year in moisture resistant packaging.

Another aspect of the present disclosure provides a composition comprising three-dimensional shapes, wherein each shape consists essentially of choline chloride, wherein the composition is obtained by a process comprising the steps of (a) providing material consisting essentially of choline chloride and (b) compacting the material to produce a solid three-dimensional shape wherein no dimension of the shape may measure more than 40 mm or less than 5 mm. In some embodiments, the composition comprises no more than 0.5% water immediately after production, as determined by Method I <921> USP 38 and/or the composition comprises no more than 0.5% water after one year of storage in moisture resistant packaging, as determined by Method I <921> USP 38. Alternatively or in addition, in some embodiments the composition does not substantially cake after storage of at least one year in moisture resistant packaging.

Another aspect of the present disclosure provides a process for producing a composition comprising three-dimensional shapes, wherein each shape consists essentially of choline chloride, the process comprising the steps of (a) providing material consisting essentially of choline chloride and (b) compacting the material to produce a solid three-dimensional shape wherein no dimension of the shape may measure more than 40 mm or less than 5 mm. In some embodiments, the process produces a composition comprising no more than 0.5% water immediately after production, as determined by Method I <921> USP 38 and/or the process produces a composition comprising no more than 0.5% water after one year of storage in moisture resistant packaging, as determined by Method I <921> USP 38. Alternatively or in addition, in some embodiments the process produces a composition that does not substantially cake after storage of at least one year in moisture resistant packaging.

DETAILED DESCRIPTION

Figure 1:
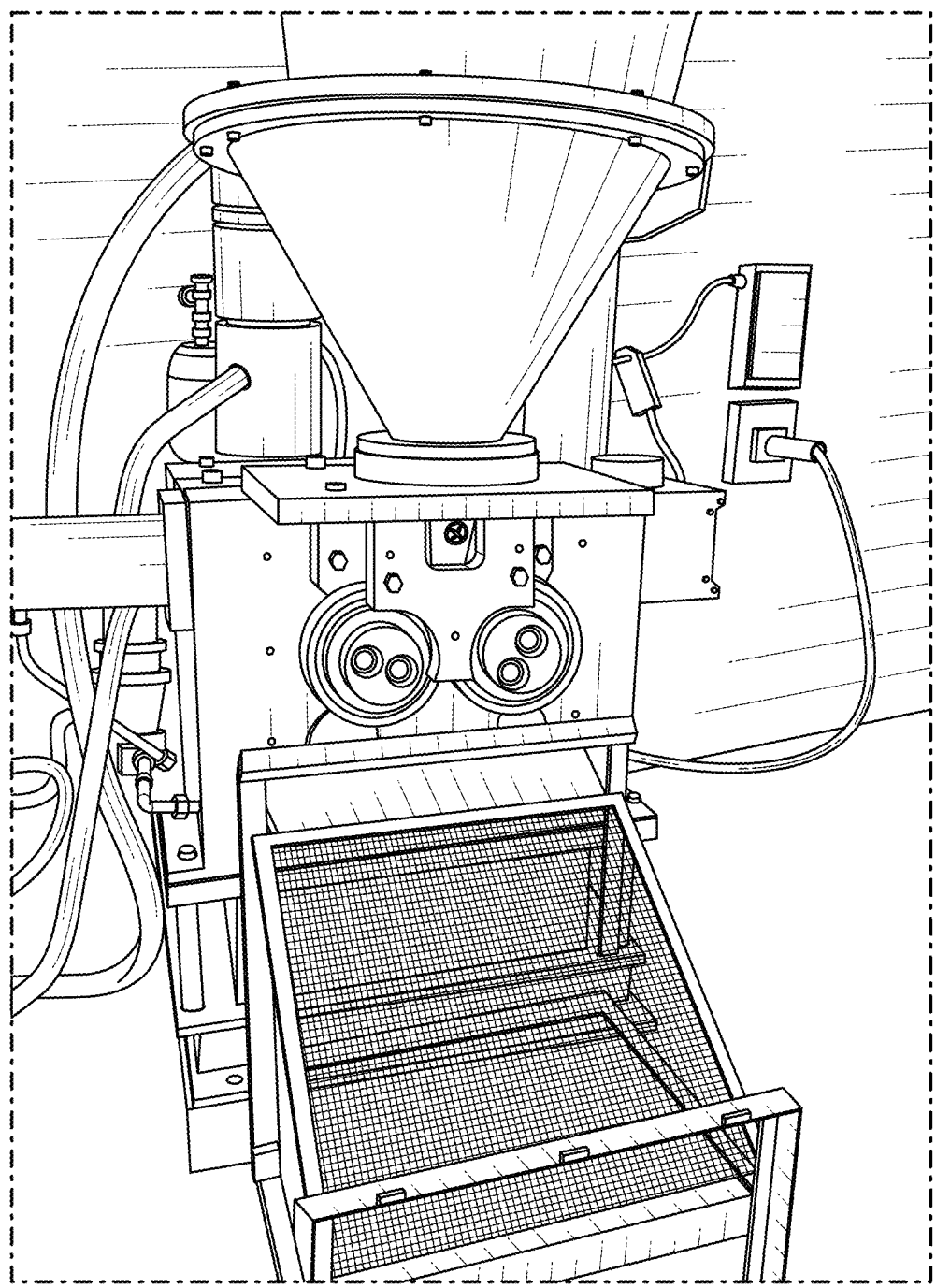
FIG. 1 is an image depicting a Hosokawa Alpine Kompaktor ARC Model CS-25 system with an angled screen with 10 mm square openings.

The present disclosure provides a composition comprising three-dimensional shapes, wherein each shape consists essentially of choline chloride. Compositions comprising these three-dimensional shapes demonstrate reduced caking, and allow operators of manufacturing and blending equipment to easily collect and measure the composition for use. Choline chloride compositions of the present invention may be agglomerated with no additives and formed to three-dimensional shapes. Additional aspects of the invention include processes for making such choline chloride compositions.

I. Compositions Comprising Choline Chloride

The present disclosure provides compositions comprising three-dimensional shapes, wherein each shape consists essentially of choline chloride.

(a) Choline Chloride

The three-dimensional shapes of the present disclosure consist essentially of choline chloride. As used herein, "consists essentially of" means the three-dimensional shapes do not have any active components other than choline chloride but may contain inactive ingredients such as minor impurities or water. In preferred embodiments, the amount of any individual impurity is no more than 0.3%, by weight (wt %), immediately after manufacture. In preferred embodiments, the amount of water is no more than 0.5 wt % immediately after manufacture. When present, these other components do not negatively impact manufacturing or processing of the composition and/or are generally regarded as safe.

In some embodiments, the three-dimensional shapes described herein may contain greater than about 90, 91, 92, 93, 94, 95, 95.5, 96, 96.5, 97, 97.1, 97.2, 97.25, 97.3, 97.4, 97.5, 97.6, 97.7, 97.75, 97.8, 97.9, 98, 98.1, 98.2, 98.25, 98.3, 98.4, 98.5, 98.6, 98.7, 98.75, 98.8, 98.9, 99, 99.1, 99.2, 99.25, 99.3, 99.4, 99.5, 99.6, 99.7, 99.75, 99.8, 99.85, 99.9, or 99.95 wt % choline chloride, calculated on the anhydrous basis. In some embodiments, a three-dimensional shape described herein may contain from about 99 wt % to about 99.95 wt %, about 99.25 wt % to about 99.95 wt %, or about 99.5 wt % to about 99.95 wt % choline chloride, calculated on the anhydrous basis. In preferred embodiments, the amount of choline chloride is at least 99.95 wt %, calculated on the anhydrous basis.

In some embodiments, three-dimensional shapes described herein contain USP-grade choline chloride. As used herein, the term "USP-grade choline chloride" refers to choline chloride as specified by the United States Pharmacopoeia 38th Revision (USP 38). USP-grade choline chloride contains no less than 99.0% and no more than 100.5% of choline chloride, calculated on the anhydrous basis, and no more than 0.5% water. Additional requirements for USP-grade choline chloride, as well as analytic tests for determining amount of choline chloride, water, impurities, etc., are set forth in the USP 38.

In alternative embodiments, choline salts other than chloride may be substituted for choline chloride.

(b) Shape

In an aspect, the three-dimensional shapes described herein may contain choline chloride uniformly distributed throughout the composition. In some embodiments, the three-dimensional shapes described herein may be formed by agglomeration. Non-limiting examples of agglomeration methods that may be used include wet agglomeration, agglomeration using heat (sintering), and pressure agglomeration. In preferred embodiments, the three-dimensional shapes described herein are formed using pressure agglomeration. Non-limiting examples of pressure agglomeration techniques that may be used include compaction, extrusion, tableting, molding, and briquetting. In preferred embodiments, the three-dimensional shapes described herein are formed by briquetting. Formation of the three-dimensional shapes described herein using briquetting is not limited to any specific briquetting process known in the art. Non-limited examples of briquetting presses that may be used herein include cylinder briquette presses, ring roller briquette presses, and roller briquette presses.

The three-dimensional shapes described herein may be cylindrical, rectangular, cubical, pyramidal, conical, or spherical. In an aspect, the three-dimensional shapes described herein may be convex or concave. In another aspect, the three-dimensional shapes described herein may be flat-faced plain, flat-faced bevel-edged, flat-faced radius edged, concave bevel-edged or any combination thereof. In some embodiments, the three-dimensional shapes described herein may be a disk, a shield, a rectangle, a stick, a cube, a triangle, an oval, a bullet, a shell, a barrel, an egg, a puck, a brick, an arrowhead, a compound cup, an arc triangle, an arc square (pillow-shaped), a diamond, a half-moon, or an almond. In preferred embodiments, the three-dimensional shapes described herein may be a pillow, an almond, or an egg.

In various embodiments, three-dimensional shapes described herein have no dimension greater than about 50 mm, about 40 mm, about 30 mm, about 20 mm, or about 10 mm. In preferred embodiments, three-dimensional shapes described herein have no dimension greater than 30 mm. For instance, no dimension may be greater than about 30 mm, about 29 mm, about 28 mm, about 27 mm, about 26 mm, about 25 mm, about 24 mm, about 23 mm, about 22 mm, about 21 mm, about 20 mm, about 19 mm, about 18 mm, about 17 mm, about 16 mm, about 15 mm, about 14 mm, about 13 mm, about 12 mm, about 11 mm, about 10 mm, about 9 mm, about 8 mm, about 7 mm, about 6 mm, or about 5 mm.

In other embodiments, three-dimensional shapes described herein may have at least two dimensions that share the same measurement. In yet other embodiments, three-dimensional shapes described herein may have at least three dimensions that share the same measurement.

In various embodiments, three-dimensional shapes described herein may have a thickness of no more than about 20 mm, about 19 mm, about 18 mm, about 17 mm, about 16 mm, or about 15 mm. In preferred embodiments, three-dimensional shapes described herein may have a thickness of no more than about 15 mm. In an aspect, three-dimensional shapes described herein may have a thickness of no more than about 15 mm, about 14.5 mm, about 14 mm, about 13.5 mm, about 13 mm, about 12.5 mm, about 12 mm, about 11.5 mm, about 11 mm, about 10.5 mm, about 10 mm, about 9.5 mm, about 9 mm, about 8.5 mm, about 8 mm, about 7.5 mm, about 7 mm, about 6.5 mm, about 6 mm, about 5.5 mm, or about 5 mm.

In various embodiments, three-dimensional shapes described herein may have a volume that measures no more than about 10 cm$^3$. Volume of a three-dimensional shape described herein may be assessed by methods known in the art. For instance, a non-limiting example of a method of measuring volume includes the buoyancy method which involves measuring the volume of the water/oil before and after immersion, and calculating the difference. In some embodiments, three-dimensional shapes described herein may have a volume no more than about 10 cm$^3$, about 9 cm$^3$, about 8 cm$^3$, about 7 cm$^3$, about 6 cm$^3$, about 5 cm$^3$, about 4 cm$^3$, about 3 cm$^3$, about 2 cm$^3$, or about 1 cm$^3$. In other embodiments, the volume of a three-dimensional shape described herein may range from about 1 cm$^3$ to about 10 cm$^3$, about 2 cm$^3$ to about 9 cm$^3$, about 3 cm$^3$ to about 8 cm$^3$, about 4 cm$^3$ to about 7 cm$^3$, or about 4.5 cm$^3$ to about 5.5 cm$^3$. In preferred embodiments, a three-dimensional shape described herein may have a volume from about 4 cm$^3$ to about 6 cm$^3$. In certain embodiments, a three dimensional shape described herein may have a volume of about 5 cm$^3$.

(c) Density

In various embodiments, three-dimensional shapes of the present disclosure may have a density of no more than about 2.0 g/cm$^3$. Density of a three-dimensional shape described herein may be assessed by methods known in the art. For example, non-limiting methods of measuring density may include use of pycnometers, hydrostatic pressure-based instruments, vibrating element transducers: ultrasonic transducers, radiation-based gauges, and buoyant force transducers. A non-limiting example of measuring density includes gas pycnometry following the method as outlined in USP 32<699> Density of Solids. In some embodiments, density may be calculated by dividing the weight of the three-dimensional shape by the volume of the shape (which can be measured as detailed above).

In some embodiments, three-dimensional shapes of the present disclosure may have a density from no more than about 2.0 g/cm$^3$ to about 0.25 g/cm$^3$, about 1.75 g/cm$^3$ to about 0.5 g/cm$^3$, about 1.5 g/cm$^3$ to about 0.75 g/cm$^3$, or about 1.25 g/cm$^3$ to about 1.0 g/cm$^3$. In other embodiments, three-dimensional shapes of the present disclosure may have a density about 2.0 g/cm$^3$, about 1.75 g/cm$^3$, about 1.5 g/cm$^3$, about 1.25 g/cm$^3$, about 1.0 g/cm$^3$, about 0.75 g/cm$^3$, about 0.5 g/cm$^3$, or about 0.25 g/cm$^3$. In still other embodiments, three-dimensional shapes of the present disclosure may have a density about 2.00 g/cm$^3$, about 1.99 g/cm$^3$, about 1.98 g/cm$^3$, about 1.97 g/cm$^3$, about 1.96 g/cm$^3$, about 1.95 g/cm$^3$, about 1.94 g/cm$^3$, about 1.93 g/cm$^3$, about 1.92 g/cm$^3$, about 1.91 g/cm$^3$, about 1.90 g/cm$^3$, about 1.89 g/cm$^3$, about 1.88 g/cm$^3$, about 1.87 g/cm$^3$, about 1.86 g/cm$^3$, about 1.85 g/cm$^3$, about 1.84 g/cm$^3$, about 1.83 g/cm$^3$, about 1.82 g/cm$^3$, about 1.81 g/cm$^3$, about 1.80 g/cm$^3$, about 1.79 g/cm$^3$, about 1.78 g/cm$^3$, about 1.77 g/cm$^3$, about 1.76 g/cm$^3$, about 1.75 g/cm$^3$, about 1.74 g/cm$^3$, about 1.73 g/cm$^3$, about 1.72 g/cm$^3$, about 1.71 g/cm$^3$, about 1.70 g/cm$^3$, about 1.69 g/cm$^3$, about 1.68 g/cm$^3$, about 1.67 g/cm$^3$, about 1.66 g/cm$^3$, about 1.65 g/cm$^3$, about 1.64 g/cm$^3$, about 1.63 g/cm$^3$, about 1.62 g/cm$^3$, about 1.61 g/cm$^3$, about 1.60 g/cm$^3$, about 1.59 g/cm$^3$, about 1.58 g/cm$^3$, about 1.57 g/cm$^3$, about 1.56 g/cm$^3$, about 1.55 g/cm$^3$, about 1.54 g/cm$^3$, about 1.53 g/cm$^3$, about 1.52 g/cm$^3$, about 1.51 g/cm$^3$, about 1.50 g/cm$^3$, about 1.49 g/cm$^3$, about 1.48 g/cm$^3$, about 1.47 g/cm$^3$, about 1.46 g/cm$^3$, about 1.45 g/cm$^3$, about 1.44 g/cm$^3$, about 1.43 g/cm$^3$, about 1.42 g/cm$^3$, about 1.41 g/cm$^3$, about 1.40 g/cm$^3$, about 1.39 g/cm$^3$, about 1.38 g/cm$^3$, about 1.37 g/cm$^3$, about 1.36 g/cm$^3$, about 1.35 g/cm$^3$, about 1.34 g/cm$^3$, about 1.33 g/cm$^3$, about 1.32 g/cm$^3$, about 1.31 g/cm$^3$, about 1.30 g/cm$^3$, about 1.29 g/cm$^3$, about 1.28 g/cm$^3$, about 1.27 g/cm$^3$, about 1.26 g/cm$^3$, about 1.25 g/cm$^3$, about 1.24 g/cm$^3$, about 1.23 g/cm$^3$, about 1.22 g/cm$^3$, about 1.21 g/cm$^3$, about 1.20 g/cm$^3$, about 1.19 g/cm$^3$, about 1.18 g/cm$^3$, about 1.17 g/cm$^3$, about 1.16 g/cm$^3$, about 1.15 g/cm$^3$, about 1.14 g/cm$^3$, about 1.13 g/cm$^3$, about 1.12 g/cm$^3$, about 1.11 g/cm$^3$, or about 1.10 g/cm$^3$.

(d) Hardness

In various embodiments, three-dimensional shapes of the present disclosure may have a hardness, measured immediately after production, of at least about 30 N. Hardness of a three-dimensional shape described herein may be assessed by methods known in the art. Non-limiting examples of methods that may be used to determine hardness include pre-stress methods, strain ramp methods, shear rate ramp methods, oscillation amplitude sweep methods, penetrometer methods, and impact-rebound methods, or instruments designed to measure the force required to break the three-dimensional shape.

In other embodiments, three-dimensional shapes of the present disclosure may have a hardness, measured immediately after production, of no less than about 40 N and no more than about 200 N, no less than about 50 N and no more than about 110 N, no less than about 60 N and no more than about 110 N, no less than about 70 N and no more than about 110 N, or no less than about 80 N and no more than about 100 N. In preferred embodiments, three-dimensional shapes of the present disclosure may have a hardness, measured immediately after production, of no less than about 40 N and no more than about 100 N. In still other embodiments, three-dimensional shapes of the present disclosure may have a hardness, measured immediately after production, of about 40 N, about 45 N, about 50 N, about 55 N, about 60 N, about 65 N, about 70 N, about 75 N, about 80 N, about 85 N, about 90 N, about 95 N, about 100 N, about 105 N, about 110 N, about 115 N, about 120 N, about 125 N, about 130 N, about 135 N, or about 140 N. In preferred embodiments, three-dimensional shapes of the present disclosure may have a hardness, measured immediately after production, of about 70 N, about 71 N, about 72 N, about 73 N, about 74 N, about 75 N, about 76 N, about 77 N, about 78 N, about 79 N, about 80 N, about 81 N, about 82 N, about 83 N, about 84 N, about 85 N, about 86 N, about 87 N, about 88 N, about 89 N, or about 80 N.

In various embodiments, three-dimensional shapes of the present disclosure may have a hardness, measured after storage, of no less than about 30 N. In other embodiments, three-dimensional shapes of the present disclosure may have a hardness, measured after storage for no less than 5 months, of no less than about 30 N. In an aspect, three-dimensional shapes of the present disclosure may be stored in moisture resistant packaging. Formats of moisture resistant packaging/containers may include, but are not limited to, multi-walled paper bags having a suitable moisture barrier, including aluminum, or fiber drums having polymeric or aluminum foil linings integral with the drum wall or loose liners inserts. Rigid containers such as blow molded drums and pails made of polymers with moisture barriers may also be used. The container may be a flexible package such as a shipping bag made of a polymer substrate. In one embodiment, the packaging may be made from aluminum foil laminated to polymer films formed from polymers that are commonly used to make moisture resistant packaging (e.g. laminates of aluminum foil with polyolefins, polyesters, styrenics or copolymers thereof). In other embodiments, the three dimensional shape may be double bagged in plastic, and stored in a box or drum.

In an aspect, three-dimensional shapes of the present disclosure may be stored in moisture resistant packaging at room temperature. It is noted that room temperature encompasses storage in non-environmentally controlled conditions, such as trucking containers, rail containers, or warehouses. In another aspect, three-dimensional shapes of the present disclosure may be stored in moisture resistant packaging at temperatures ranging from about 15° C. to about 30° C. In yet another aspect, three-dimensional shapes of the present disclosure may be stored in moisture resistant packaging at temperatures ranging from about 20° C. to about 25° C. In some aspects, three-dimensional shapes of the present disclosure may be stored in moisture resistant packaging at about 15° C., about 16° C., about 17° C., about 18° C., about 19° C., about 20° C., about 21° C. about 22° C., about 23° C., about 24° C., about 25° C., about 26° C., about 27° C., about 28° C., about 29° C., or about 30° C. In some embodiments, three-dimensional shapes of the present disclosure may have a hardness, measured after storage for about 1 month to about 5 months, of less than about 30 N. In an aspect, three-dimensional shapes of the present disclosure may have a hardness of no less than about 30 N after storage for about 1 month, about 2 months, about 3 months, about 4 months, or about 5 months. In another aspect, three-dimensional shapes of the present disclosure may have a hardness of from about 30 N to about 200N after storage for about 1 month, about 2 months, about 3 months, about 4 months, or about 5 months. In still another aspect, three-dimensional shapes of the present disclosure may have a hardness of about 30 N, about 40 N, about 50 N, about 60 N, about 70 N, about 80 N, about 90 N, about 100 N, about 110 N, about 120 N, about 130 N, or about 140 N after storage for about 1 month, about 2 months, about 3 months, about 4 months, or about 5 months. In yet another aspect, three-dimensional shapes of the present disclosure may have a hardness of about 40 N, about 41 N, about 42 N, about 43 N, about 44 N, about 45 N, about 46 N, about 47 N, about 48 N, about 49 N, about 50 N, about 51 N, about 52 N, about 53 N, about 54 N, about 55 N, about 56 N, about 57 N, about 58 N, about 59 N, about 60 N, about 61 N, about 62 N, about 63 N, about 64 N, about 65 N, about 66 N, about 67 N, about 68 N, about 69 N, about 70 N, about 71 N, about 72 N, about 73 N, about 74 N, about 75 N, about 76 N, about 77 N, about 78 N, about 79 N, about 80 N, about 81 N, about 82 N, about 83 N, about 84 N, about 85 N, about 86 N, about 87 N, about 88 N, about 89 N, about 90 N, about 91 N, about 92 N, about 93 N, about 94 N, about 95 N, about 96 N, about 97 N, about 98 N, about 99 N, about 100 N, about 101 N, about 102 N, about 103 N, about 104 N, about 105 N, about 106 N, about 107 N, about 108 N, about 109 N, about 110 N, about 111 N, about 112 N, about 113 N, about 114 N, about 115 N, about 116 N, about 117 N, about 118 N, about 119 N, about 120 N, about 121 N, about 122 N, about 123 N, about 124 N, about 125 N, about 126 N, about 127 N, about 128 N, about 129 N, about 130 N, about 131 N, about 132 N, about 133 N, about 134 N, about 135 N, about 136 N, about 137 N, about 138 N, about 139 N, about 140 N, about 150 N, about 160 N, about 170 N, about 180 N, about 190 N, or about 200 N after storage for about 1 month, about 2 months, about 3 months, about 4 months, or about 5 months. In preferred embodiments, three-dimensional shapes of the present disclosure may have a hardness of about 40 N to about 200 N after 5 months of storage.

(e) Compression Force

As used herein, "compression force" refers to the amount of force required to form a three-dimensional shape as described in the present disclosure. In various embodiments, three-dimensional shapes of the present disclosure may be formed with compression force of at least about 25 kN. Compression force may be assessed by methods known in the art. Non-limiting examples of methods that may be used to determine compression force include direct force measurement and force shunt measurement. In some embodiments, equipment used to create the three-dimensional shapes may monitor compression force.

In other embodiments, three-dimensional shapes of the present disclosure may be formed with compression force of no less than about 25 kN and no more than about 150 kN, no less than about 30 kN and no more than about 145 kN, no less than about 35 kN and no more than about 140 kN, or no less than about 40 kN and no more than about 135 kN. In preferred embodiments, three-dimensional shapes of the present disclosure may be formed with compression force of no less than about 60 kN and no more than about 120 kN. In still other embodiments, three-dimensional shapes of the present disclosure may be formed with compression force of about 25 kN, about 30 kN, about 35 kN, about 40 kN, about 45 kN, about 50 kN, about 55 kN, about 60 kN, about 65 kN, about 70 kN, about 75 kN, about 80 kN, about 85 kN, about 90 kN, about 95 kN, about 100 kN, about 105 kN, about 110 kN, about 115 kN, about 120 kN, about 125 kN, about 130 kN, about 135 kN, about 140 kN, about 145 kN, or about 150 kN. In preferred embodiments, three-dimensional shapes of the present disclosure may be formed with compression force of about 50 kN to about 100 kN. In a preferred aspect, the compression force used to form three-dimensional shapes of the present disclosure is about 80 kN.

(f) Low Agglomeration/Caking

Three-dimensional shapes of the present disclosure do not exhibit significant agglomeration between the shapes and retain this attribute after storage under suitable conditions. Stated another way, compositions comprising three-dimensional shapes of the present disclosure do not substantially cake upon storage. As used herein, the phrase "does not substantially cake" refers to the ability of a three-dimensional shape, when stored in aggregate, to substantially avoid fusion to an adjacent three-dimensional shape. In this context, the phrase "substantially avoid fusion" means that a three-dimensional shape can be separated from an adjacent shape using only minimal physical manipulation, such as shaking or knocking the container by hand.

Suitable storage conditions includes storage in moisture resistant packaging. Formats of moisture resistant packaging/containers may include, but are not limited to, multi-walled paper bags having a suitable moisture barrier, including aluminum, or fiber drums having polymeric or aluminum foil linings integral with the drum wall or loose liner inserts. Rigid containers such as blow molded drums and pails made of polymers with moisture barriers may also be used. The container may be a flexible package such as a shipping bag made of a polymer substrate. In one embodiment, the packaging may be made from aluminum foil laminated to polymer films formed from polymers that are commonly used to make moisture resistant packaging (e.g. laminates of aluminum foil with polyolefins, polyesters, styrenics or copolymers thereof). In an aspect, a composition comprising three-dimensional shapes of the present disclosure may be stored in moisture resistant packaging at room temperature. It is noted that room temperature encompasses storage in non-environmentally controlled conditions, such as trucking containers, rail containers, or warehouses. In another aspect, three-dimensional shapes of the present disclosure may be stored in moisture resistant packaging at temperatures ranging from about 15° C. to about 30° C. In yet another aspect, three-dimensional shapes of the present disclosure may be stored in moisture resistant packaging at temperatures ranging from about 20° C. to about 25° C. In some aspects, three-dimensional shapes of the present disclosure may be stored in moisture resistant packaging at about 15° C., about 16° C., about 17° C., about 18° C., about 19° C., about 20° C., about 21° C. about 22° C., about 23° C., about 24° C., about 25° C., about 26° C., about 27° C., about 28° C., about 29° C., or about 30° C. In another aspect, a composition comprising three-dimensional shapes of the present disclosure may be stored in moisture resistant packaging at temperatures ranging from about 20° C. to about 25° C. In some aspects, a composition comprising three-dimensional shapes of the present disclosure may be stored in moisture resistant packaging at about 20° C., about 21° C. about 22° C., about 23° C., about 24° C., or about 25° C.

In various embodiments, a composition comprising three-dimensional shapes of the present disclosure does not substantially cake after no less than about 2 years of storage under the conditions described in this section. In still other embodiments, a composition comprising three-dimensional shapes of the present disclosure does not substantially cake after no less than about 1 year of storage under the conditions described in this section. In certain embodiments, a composition comprising three-dimensional shapes of the present disclosure does not substantially cake after no less than about 12 months, 11 months, 10 months, 9 months, 8 months, 7 months, 6 months, 5 months, 4 months, 3 months, 2 months, or 1 month of storage under the conditions described in this section.

(g) Dissolution Time

In various embodiments, choline chloride formed into three-dimensional shapes of the present disclosure may have a dissolution time that makes the composition easy to work with. As used herein, "dissolution time" is the amount of time that it takes to completely dissolve a three-dimensional shape of the present disclosure, visually, using USP Dissolution Apparatus II (paddles) at 100 rpm in 900 mL of water at 37° C. In other embodiments, choline chloride formed into three-dimensional shapes of the present disclosure may have a dissolution time of about 30 seconds to 10 minutes. In an aspect, choline chloride formed into three-dimensional shapes of the present disclosure may have a dissolution time of about 30 seconds to about 1 minute, 1 minute to about 10 minutes, about 1 minutes to about 9 minutes, or about 1 minutes to about 8 minutes about 1 minute to about 7 minutes, about 1 minute to about 6 minutes, about 1 minute to about 5 minutes, about 1 minute to about 4 minutes, about 1 minute to about 3 minutes, or about 1 minute to about 2 minutes. In another aspect, choline chloride formed into three-dimensional shapes of the present disclosure may have a dissolution time of about 30 seconds, 1 minute, about 1.5 minutes, about 2 minutes, about 2.5 minutes, about 3 minutes, about 3.5 minutes, about 4 minutes, about 4.5 minutes, about 5 minutes, about 5.5 minutes, about 6 minutes, about 6.5 minutes, about 7 minutes, about 7.5 minutes, about 8 minutes, about 8.5 minutes, about 9 minutes, about 9.5 minutes or about 10 minutes.

(h) Water Content

In another aspect, a composition comprising three-dimensional shapes of the present disclosure contains no more than 0.5% water. Stated another, the total water content is less than or equal to 0.5%. Preferably, the total water content is about 0.3% or less, more preferably about 0.25% or less, even more preferably about 0.2% or less. In certain embodiments, the total water content is about 0.2% or less. In other embodiments, the total water content is about 0.15% or less. In still other embodiments, the total water content is about 0.1% or less. Total water content may be determined by Method I <921> USP 38, including Method 1a (Direct Titration), Method 1b (Residual Titration), and Method 1c (Coulometric Titration). In an exemplary method, total water content is determined by high-temperature colorimetric detection of water, for example, using a Berghof EasH$_2$O® instrument.

In some embodiments, a composition comprising three-dimensional shapes of the present disclosure contains no more than 0.5% water after no less than about 12 months, 11 months, 10 months, 9 months, 8 months, 7 months, 6 months, 5 months, 4 months, 3 months, 2 months, or 1 month of storage in moisture resistant packaging at temperatures ranging from about 15° C. to about 30° C., or about 20° C. to about 25° C.

In some embodiments, a composition comprising three-dimensional shapes of the present disclosure contains no more than 0.5% water after no less than about 24 months, 21 months, 18 months, 15 months, or 12 months of storage in moisture resistant packaging at temperatures ranging from about 15° C. to about 30° C., or about 20° C. to about 25° C.

In some embodiments, a composition comprising three-dimensional shapes of the present disclosure contains no more than 0.5% water after no less than about 12 months, 11 months, 10 months, 9 months, 8 months, 7 months, 6 months, 5 months, 4 months, 3 months, 2 months, or 1 month of storage in moisture resistant packaging at temperatures ranging from about 25° C. to about 40° C. with 75% relative humidity.

(i) Storage Ability

In some aspects, a composition comprising three-dimensional shapes of the present disclosure have improved storage ability. As used herein, "storage ability" refers to the ability of a material to resist caking for a prolonged period of time. In various embodiments, a composition comprising three-dimensional shapes of the present disclosure may have storage ability of at least about 1 month. In an aspect, the storage ability of a composition comprising three-dimensional shapes of the present disclosure may be from about 1 month to about 2.5 years, about 1 month to about 2 years, about 1 month to about 1.5 years, about 1 month to about 1 year, about 1 month to about 6 months, or about 1 month to about 3 months. In other embodiments, a composition comprising three-dimensional shapes of the present disclosure may have storage ability of at least about 1 month in room temperature. In an aspect, the storage ability of a composition comprising three-dimensional shapes of the present disclosure may be from about 1 month to about 3 years, about 1 month to about 2.5 years, about 1 month to about 2 years, about 1 month to about 1.5 years, about 1 month to about 1 year, about 1 month to about 6 months, or about 1 month to about 3 months in room temperature. In still other embodiments, a composition comprising three-dimensional shapes of the present disclosure may have storage ability of at least about 1 month in moisture resistant packaging. Formats of moisture resistant packaging/containers may include, but are not limited to, multi-walled paper bags having a suitable moisture barrier, including aluminum, or fiber drums having polymeric or aluminum foil linings integral with the drum wall or loose liners inserts. Rigid containers such as blow molded drums and pails made of polymers with moisture barriers may also be used. The container may be a flexible package such as a shipping bag made of a polymer substrate. In one embodiment, the packaging may be made from aluminum foil laminated to polymer films formed from polymers that are commonly used to make moisture resistant packaging (e.g. laminates of aluminum foil with polyolefins, polyesters, styrenics or copolymers thereof). In an aspect, the storage ability of a composition comprising three-dimensional shapes of the present disclosure may be from about 1 month to about 2.5 years, about 1 month to about 2 years, about 1 month to about 1.5 years, about 1 month to about 1 year, about 1 month to about 6 months, or about 1 month to about 3 months when stored in moisture resistant packaging.

(j) Other Components

In another aspect, a composition comprising three-dimensional shapes of the present disclosure may or may not contain components in addition, or in alternative to, choline chloride and water. When present, these other components do not negatively impact manufacturing or processing of the composition and/or are generally regarded as safe.

For instance, in some embodiments, a composition comprising three-dimensional shapes of the present disclosure may comprise one or more choline salt(s) other than choline chloride. Non-limiting examples of such choline salts may include choline bitartrate, choline dihydrogen citrate or choline carbonate.

Advantageously, a composition comprising three-dimensional shapes of the present disclosure may lack agents that are used by the pharmaceutical and food industries to promote powder flow and to reduce the caking or clumping that can occur when powders are stored in bulk, during the emptying of powder hoppers, or during powder processing. These agents may be referred to by a number of different names including, but not limited to, diluents, glidants, lubricants, binders, encapsulating agents, carriers, flow agents, or anticaking agents, and may work in a variety of different ways.

In some embodiments, a composition comprising three-dimensional shapes of the present disclosure (a) does not contain an excipient that has a higher affinity for water than choline chloride, (b) the composition does not contain choline chloride that has been coated, encapsulated or treated to increase its hydrophobicity, (c) the composition does not contain a carrier or a binder to stabilize the particles size of the choline chloride, (d) the composition does not contain a volatile alcohol; or any combination of (a) to (d).

In some embodiments, a composition comprising three-dimensional shapes of the present disclosure is additive-free. As used herein the term "additive-free" means lacking agents generally regarded as safe for human consumption that are used by the pharmaceutical and food industries to promote powder flow and to reduce the caking or clumping that can occur when powders are stored in bulk, during the emptying of powder hoppers, or during powder processing. These agents may be referred to by a number of different names including, but not limited to, diluents, glidants, lubricants, binders, encapsulating agents, carriers, or anticaking agents. Non-limiting examples of these agents include carbonates (e.g., sodium carbonates, potassium carbonates, ammonium carbonates, magnesium carbonates, calcium carbonate, ferrous carbonate, etc.), chlorides (e.g., potassium chloride, ammonium chloride, magnesium chloride, stannous chloride, etc., with the exception of choline chloride), hydroxides of alkali metals (e.g., sodium hydroxide, potassium hydroxide, calcium hydroxide, ammonium hydroxide, magnesium hydroxide, etc.), sugar alcohols (e.g., lactitol, maltitol, mannitol, sorbitol, etc.), fatty acids or salts thereof (e.g., stearic acid, magnesium stearate, calcium stearate, zinc stearate, etc.), calcium oxide, magnesium oxide, hydrochloric acid, ammonia solution, sulfuric acid, sodium sulfate, potassium sulfate, calcium sulfate, ammonium sulfate, magnesium sulfate, copper(II) sulfate, aluminium sulfate, aluminium sodium sulfate, aluminium potassium sulfate, aluminium ammonium sulfate, synthetic calcium aluminates, sodium ferrocyanide, potassium ferrocyanide, ferrous hexacyanomanganate, calcium ferrocyanide, ferrous lactate, sodium thiosulfate, dicalcium diphosphate, sodium aluminium phosphate, calcium phosphate, tricalcium phosphate, calcium sodium polyphosphate, calcium polyphosphate, ammonium polyphosphate, sodium silicates, silicon dioxide (silica), calcium silicate, magnesium silicate, talc, sodium aluminosilicate, potassium aluminium silicate, calcium aluminosilicate, zinc silicate, bentonite, aluminium silicate (kaolin), potassium silicate, vermiculite, sepiolite, sepiolitic clay, lignosulphonates, natrolite-phonolite, gluconic acid and salts thereof (e.g. sodium gluconate, potassium gluconate, calcium gluconate, ferrous gluconate, magnesium gluconate, glucono delta-lactone, etc.), 4-hexylresorcinol antioxidant, perlite, microcrystalline cellulose, powdered cellulose, alpha cellulose, starch, dextrates, dextrins, dextrose, fructose, maltose, mannose, sucrose, lactose, syrup, glyceryl behenate, mineral oil, sodium lauryl sulfate, sodium stearyl fumarate, hydrogenated vegetable oil, polyethylene oxide, polyethylene glycol, sodium benzoate, acacia, alginic acid, ammonio methacrylate copolymer, carbomer copolymer, carbomer homopolymer, carbomer interpolymer, sodium carboxymethylcelulose, copovidone, ethylcellulose, gelatin, glucose, guar gum, hydroxypropyl cellulose, hypromellose, hypromellose acetate succinate, methylcellulose, and povidone.

(k) Preferred Embodiments

In some embodiments, a composition comprises a plurality of three-dimensional shapes, as described above, wherein the composition meets USP 38 standards for choline chloride at the time of manufacture and after no less than about 12 months, 11 months, 10 months, 9 months, 8 months, 7 months, 6 months, 5 months, 4 months, 3 months, 2 months, or 1 month of storage in moisture resistant packaging at temperatures ranging from about 15° C. to about 30° C., or about 20° C. to about 25° C.

In some embodiments, a composition comprises a plurality of three-dimensional shapes, as described above, wherein the composition meets USP 38 standards for choline chloride at the time of manufacture and after no less than about 24 months, 21 months, 18 months, 15 months, or 12 months of storage in moisture resistant packaging at temperatures ranging from about 15° C. to about 30° C., or about 20° C. to about 25° C.

In some embodiments, a composition comprises a plurality of three-dimensional shapes, as described above, wherein the composition meets USP 38 standards for choline chloride at the time of manufacture and after no less than about 12 months, 11 months, 10 months, 9 months, 8 months, 7 months, 6 months, 5 months, 4 months, 3 months, 2 months, or 1 month of storage in moisture resistant packaging at temperatures ranging from about 25° C. to about 40° C. with 75% relative humidity.

In further embodiments of each of the above, no dimension of each shape may measure more than 40 mm or less than 5 mm, more than 30 mm or less than 10 mm, or more than 30 mm or less than 20 mm. In still further embodiments, the density of each shape is no more than about 2.0 g/cm$^3$ and/or the volume of each shape is no more than about 10 cm$^3$. In exemplary embodiments, each shape may be a pillow.

II. Methods of Preparing a Composition Comprising a Three-Dimensional Shape Described Herein The present disclosure provides methods/processes of preparing the three-dimensional shapes as disclosed herein. Choline chloride three-dimensional shapes of this disclosure may be produced using roller compaction methods known in the art. As used herein, "roller compaction" and "briquetting" are both terms used herein to refer to the preferred process of preparing choline chloride three-dimensional shapes of the present disclosure. In roller compaction, powder or granular material is fed to two counter-rotating rolls which draws the material between the rolls due to friction and compacts the material in the absence of water into a three-dimensional shape.

(a) Shape

In various embodiments, three-dimensional shapes of the present disclosure may be formed by one or more methods of briquetting known in the art. Roller designs and roller configurations known in the art for briquetting processes may be used, as long as the three-dimensional shape meets the requirements detailed above in section I. The three-dimensional shapes of the present disclosure will depend on the surface profile of the roller. The three-dimensional shapes of the present disclosure may be as described in section I above.

(b) Press Force

In various embodiments, three-dimensional shapes of the present disclosure may be formed by one or more methods of briquetting known in the art wherein the press force may be no more than about 120 kN. In an aspect, three-dimensional shapes of the present disclosure may be formed by a briquetting process wherein the press force may be about 120 kN to about 20 kN, about 110 kN to about 30 kN, about 100 kN to about 40 kN, or about 90 kN to about 50 kN. In another aspect, three-dimensional shapes of the present disclosure may be formed by a briquetting process wherein the press force may be about 120 kN, about 110 kN, about 100 kN, about 90 kN, about 80 kN, about 70 kN, about 60 kN, about 50 kN, about 40 kN, about 30 kN, or about 20 kN. In a preferred aspect, three-dimensional shapes of the present disclosure may be formed by a briquetting process wherein the press force may be about 90 kN, about 88 kN, about 86 kN, about 84 kN, about 82 kN, about 80 kN, about 78 kN, about 76 kN, about 74 kN, about 72 kN, or about 70 kN.

In other embodiments, three-dimensional shapes of the present disclosure may be formed by one or more methods of briquetting known in the art wherein the constant press force may be no more than about 120 kN. In an aspect, three-dimensional shapes of the present disclosure may be formed by a briquetting process wherein the constant press force may be about 120 kN to about 20 kN, about 110 kN to about 30 kN, about 100 kN to about 40 kN, or about 90 kN to about 50 kN. In another aspect, three-dimensional shapes of the present disclosure may be formed by a briquetting process wherein the constant press force may be about 120 kN, about 110 kN, about 100 kN, about 90 kN, about 80 kN, about 70 kN, about 60 kN, about 50 kN, about 40 kN, or about 30 kN about 20 kN. In a preferred aspect, three-dimensional shapes of the present disclosure may be formed by a briquetting process wherein the constant press force may be about 90 kN, about 88 kN, about 86 kN, about 84 kN, about 82 kN, about 80 kN, about 78 kN, about 76 kN, about 74 kN, about 72 kN, or about 70 kN.

In other embodiments, three-dimensional shapes of the present disclosure may be formed by one or more methods of briquetting known in the art wherein the initial press force may be no more than about 120 kN. In an aspect, three-dimensional shapes of the present disclosure may be formed a briquetting process wherein the initial press force may be about 120 kN to about 20 kN, about 110 kN to about 30 kN, about 100 kN to about 40 kN, or about 90 kN to about 50 kN. In another aspect, three-dimensional shapes of the present disclosure may be formed a briquetting process wherein the initial press force may be about 120 kN, about 110 kN, about 100 kN, about 90 kN, about 80 kN, about 70 kN, about 60 kN, about 50 kN, about 40 kN, or about 30 kN about 20 kN. In a preferred aspect, three-dimensional shapes of the present disclosure may be formed a briquetting process wherein the initial press force may be about 90 kN, about 88 kN, about 86 kN, about 84 kN, about 82 kN, about 80 kN, about 78 kN, about 76 kN, about 74 kN, about 72 kN, or about 70 kN.

In yet other embodiments, three-dimensional shapes of the present disclosure may be formed by one or more methods of briquetting known in the art wherein the intermediate press force may be no more than about 120 kN. In an aspect, three-dimensional shapes of the present disclosure may be formed by a briquetting process wherein the intermediate press force may be about 120 kN to about 20 kN, about 110 kN to about 30 kN, about 100 kN to about 40 kN, or about 90 kN to about 50 kN. In another aspect, three-dimensional shapes of the present disclosure may be formed by a briquetting process wherein the intermediate press force may be about 120 kN, about 110 kN, about 100 kN, about 90 kN, about 80 kN, about 70 kN, about 60 kN, about 50 kN, about 40 kN, or about 30 kN about 20 kN. In a preferred aspect, three-dimensional shapes of the present disclosure may be formed by a briquetting process wherein the intermediate press force may be about 90 kN, about 88 kN, about 86 kN, about 84 kN, about 82 kN, about 80 kN, about 78 kN, about 76 kN, about 74 kN, about 72 kN, or about 70 kN.

In still other embodiments, three-dimensional shapes of the present disclosure may be formed by one or more methods of briquetting known in the art wherein the final press force may be no more than about 120 kN. In an aspect, three-dimensional shapes of the present disclosure may be formed by a briquetting process wherein the final press force may be about 120 kN to about 20 kN, about 110 kN to about 30 kN, about 100 kN to about 40 kN, or about 90 kN to about 50 kN. In another aspect, three-dimensional shapes of the present disclosure may be formed by a briquetting process wherein the final press force may be about 120 kN, about 110 kN, about 100 kN, about 90 kN, about 80 kN, about 70 kN, about 60 kN, about 50 kN, about 40 kN, about 30 kN, or about 20 kN. In a preferred aspect, three-dimensional shapes of the present disclosure may be formed by a briquetting process wherein the final press force may be about 90 kN, about 88 kN, about 86 kN, about 84 kN, about 82 kN, about 80 kN, about 78 kN, about 76 kN, about 74 kN, about 72 kN, or about 70 kN.

(c) Yield (Fines)

In various embodiments, three-dimensional shapes of the present disclosure may be formed by one or more methods of briquetting known in the art wherein the yield of the composition may be no less than about 80%, wherein yield is calculated by 100-% fines. In other embodiments, three-dimensional shapes of the present disclosure may be formed by one or more methods of briquetting known in the art wherein the yield of the composition may range from about 80% to about 99.9%, about 85% to about 99.5%, about 85.5% to about 99%, about 86% to about 98.5%, about 86.5% to about 98%, about 87% to about 97.5%, about 87.5% to about 97%, about 88% to about 96.5%, about 88.5% to about 96%, or about 89% to about 95.5%. In an aspect, three-dimensional shapes of the present disclosure may be formed by one or more methods of briquetting with a yield about 80%, about 80.5%, about 81%, about 81.5%, about 82%, about 82.5%, about 83%, about 83.5%, about 84%, about 84.5%, about 85%, about 85.5%, about 86%, about 86.5%, about 87%, about 87.5%, about 88%, about 88.5%, about 89%, about 89.5%, about 90%, about 90.5%, about 91%, about 91.5%, about 92%, about 92.5%, about 93%, about 93.5%, about 94%, about 94.5%, about 95%, about 95.5%, about 96%, about 96.5%, about 97%, about 97.5%, about 98%, about 98.5%, about 99%, about 99.5%, or about 99.9%. In preferred embodiments, methods of the present disclosure may yield about 90% of three-dimensional shapes of the present disclosure.

In various embodiments, three-dimensional shapes of the present disclosure may be formed by one or more methods of briquetting known in the art such that excessive fines are not produced. As used herein, "fines" refers to the materials that do not get compacted into the final three-dimensional shape. Such fines would need to be reworked and represent an inefficiency in the compaction process or would be considered a loss of product. Percent fines were determined herein by weighing the remaining particles (fines) not in a three-dimensional shape after compaction and screening of the three-dimensional shapes divided by the weight of fines+the weight of the three-dimensional shapes multiplied by 100.

In various embodiments, three-dimensional shapes of the present disclosure may be formed by one or more methods of briquetting known in the art such that the amount of fines produced may be no more than about 20%. In other embodiments, three-dimensional shapes of the present disclosure may be formed by one or more methods of briquetting known in the art such that the amount of fines produced may range from about 0.5% to about 20% fines, about 1% to about 15% fines, about 1.5% to about 10% fines, or about 2% to about 10% fines. In other embodiments, methods of the present disclosure may produce three-dimensional shapes of the present disclosure with about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 9%, about 9.5% about 10%, about 10.5%, about 11%, about 11.5% about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, or about 20% fines. In preferred embodiments, methods of the present disclosure may produce three-dimensional shapes of the present disclosure with less than about 10% fines.

III. Enumerated Embodiments

The following enumerated embodiments are presented to illustrate certain aspects of the present invention, and are not intended to limit its scope.

1. A composition comprising three-dimensional shapes, wherein each shape consists essentially of choline chloride, and no dimension of each shape may measure more than 40 mm or less than 5 mm.

2. The composition of embodiment 1, wherein the three-dimensional shape is selected from the group consisting of spheres, cones, disks, shields, rectangles, sticks, cubes, triangles, ovals, bullets, shells, barrels, eggs, pucks, bricks, arrowheads, compound cups, arc triangles, pillows, diamonds, half-moons, and almonds.

3. The composition of any of the above embodiments, wherein each shape has a uniform density.

4. The composition of any of the above embodiments, wherein the density of each shape is no more than about 2.0 g/cm$^3$.

5. The composition of any of the above embodiments, wherein the volume of each shape is no more than about 10 cm$^3$.

6. The composition of any of the above embodiments, wherein the hardness of each shape as measured immediately after production is at least about 40 N.

7. The composition of any of the above embodiments, wherein the hardness of each shape as measured after about 6 months of storage is at least about 40 N.

8. The composition of any of the above embodiments, wherein no more than 20% fines (product not compacted into three-dimensional form) remain from the compaction process.

9. The composition of any of the above embodiments, wherein the visual dissolution time of each shape is no more than about 10 minutes using USP Apparatus II (paddles), at 100 rpm, in 900 mL of water at 37° C.

10. The composition of any of the above embodiments, wherein the composition comprises no more than 0.5% water immediately after production, as determined by Method I <921> USP 38.

11. The composition of any of the above embodiments, wherein the composition comprises no more than 0.5% water after one year of storage in moisture resistant packaging, as determined by Method I <921> USP 38.

12. The composition of any of the above embodiments, wherein the composition does not substantially cake after storage of at least one year in moisture resistant packaging.

13. A composition comprising three-dimensional shapes, wherein each shape consists essentially of choline chloride, wherein the composition is obtained by a process comprising the steps of (a) providing material consisting essentially of choline chloride and (b) compacting the material to produce a solid three-dimensional shape wherein no dimension of the shape may measure more than 40 mm or less than 5 mm.

14. The composition of embodiment 13, wherein the composition does not substantially cake after storage of at least one year in moisture resistant packaging.

15. The composition of embodiment 13, wherein the three-dimensional shape is selected from the group consisting of spheres, cones, disks, shields, rectangles, sticks, cubes, triangles, ovals, bullets, shells, barrels, eggs, pucks, bricks, arrowheads, compound cups, arc triangles, pillows, diamonds, half-moons, and almonds.

16. The composition of any of embodiments 13-15, wherein the density of each shape is uniform.

17. The composition of any of embodiments 13-16, wherein the density of each shape is no more than about 2.0 g/cm$^3$.

18. The composition of any of embodiments 13-17, wherein the volume of each shape is no more than about 10 cm$^3$.

19. The composition of any of embodiments 13-18, wherein the hardness of each shape as measured immediately after production is at least about 40 N.

20. The composition of any of embodiments 13-19, wherein the hardness of each shape as measured after about 6 months of storage is at least about 40 N.

21. The composition of any of embodiments 13-21, wherein the composition comprises no more than 20% fines (product not compacted into three-dimensional form) after the compaction process.

22. The composition of any of embodiments 13-22, wherein the visual dissolution time of each shape is no more than about 10 minutes using USP Apparatus II (paddles), at 100 rpm, in 900 mL of water at 37° C.

23. The composition of any of embodiments 13-22, wherein the composition comprises no more than 0.5% water immediately after production, as determined by Method I <921> USP 38.

24. The composition of any of embodiments 13-23, the composition comprises no more than 0.5% water after one year of storage in moisture resistant packaging, as determined by Method I <921> USP 38.

25. A process for producing a composition comprising three-dimensional shapes, wherein each shape consists essentially of choline chloride, the process comprising the steps of (a) providing material consisting essentially of choline chloride and (b) compacting the material to produce a solid three-dimensional shape wherein no dimension of the shape may measure more than 40 mm or less than 5 mm.

26. The process of embodiment 25, wherein a roll type briquette machine is used in step (b) to compact the material.

27. The process of any of embodiments 25-26, wherein the three-dimensional shape is selected from the group consisting of spheres, cones, disks, shields, rectangles, sticks, cubes, triangles, ovals, bullets, shells, barrels, eggs, pucks, bricks, arrowheads, compound cups, arc triangles, pillows, diamonds, half-moons, and almonds.

28. The process of any of embodiments 25-27, wherein the press force is no more than about 120 kN.

29. The process of any of embodiments 25-28, wherein the yield of the composition may be no less than about 80%.

30. The process of any of embodiments 25-29, wherein the amount of fines produced may be no more than about 20%.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Almond-shaped three-dimensional shapes of choline chloride were formed to determine if briquetting the material reduces the surface area sufficiently to limit the materials ability to absorb moisture and/or minimize or eliminate caking of the product. Almond-shaped three-dimensional shapes of choline chloride were formed using a Hosokawa Alpine Kompaktor ARC Model CS-25 system (hereinafter "the CS-25"). Material was manually charged into a feed hopper where a cylindrical feed screw was installed in the feed hopper. The screw also had a scraper with close clearance to the hopper wall. The feed screw was used to meter the material into the compaction area (nip area) that is located between two counter rotating compacting rolls. The material was then compressed by the two rotating compacting rolls. The rolls consisted of two rows of almond-shaped openings with sizes of 30 mm×20 mm×14 mm. The speed of the rolls and feed screw were adjusted to affect the hardness of the flakes. The CS-25 was equipped with a hydraulic device to maintain pressure on the rolls. A maximum hydraulic pressure of 80 bar was set for the test. As the three-dimensional shapes were discharged from the rolls, they fell onto an angled screen with 10 mm square openings (FIG. 1). This was done to help break off the connecting material between the three-dimensional shapes and remove any fines from the product.

A total of six tests were conducted to produce almond-shaped three-dimensional shapes of choline chloride. For Test 1, the initial press force target was 10 kilonewtons (kN). The CS-25 was run with a roll speed of 2.1 rpm and screw speed of 15 rpm. This produced a press force of about 60 kN. It was decided to continue the test with the higher press force. After about 3.75 minutes, the collection bin was swapped out as the product had some visible contaminants in it, likely due to some residue of the previous material run. For the second half of the run the press force decreased to 50 kN. Therefore there were two products from Test 1: 1A and 1B. The three-dimensional shapes from both products were hard and shiny. A briquette from 1A was placed in water to determine how long it would take to dissolve, which was approximately 4 minutes.

For Test 2 a press force of 30 kN was targeted. This was accomplished with a roll speed of 3 rpm and screw speed of 18.5 rpm. The three-dimensional shapes from this test were not as hard as the previous run and the time to dissolve in water was much faster, approximately 2.5 minutes.

A higher press force of 90 kN was targeted for Test 3 however with a roll speed of 2.1 rpm and screw speed of 21 rpm, the press force turned out to be about 100 kN. The result was hard, shiny three-dimensional shapes, which took about 4 to dissolve in water.

For Test 4 an attempt was made to achieve a press force of 130 kN, however even with the minimum roll speed of 2.1 rpm and increasing the screw speed it was not possible to increase the press force over 115 kN. A larger screw might allow for more material to be pushed into the nip, therefore resulting in a higher press force.

At this point it was decided to conduct two extended runs to produce sufficient material to fill fiber drums. The purpose was to see how the briquetted material would change after being shipped in a drum. For Test 5, a 60 kN press force was used. This was achieved with a roll speed of 2.1 rpm and an initial screw speed of 15 rpm. Over the course of the run, the screw speed was varied to maintain the press force at about 60 kN. The run took 47.9 minutes to produce 77.3 pounds of three-dimensional shapes. In addition, 5.17 pounds of "fines" were produced; therefore, the product yield was 93.7%. The product capacity for this run was 96.8 pounds per hour. The three-dimensional shapes from this run were used to fill one of the drums, the excess was kept separate. The three-dimensional shapes were double bagged and closed with zip ties. Desiccant bags were placed between the two liners. The drum lid was then secured with clear packing tape.

A press force of around 100 kN was maintained for Test 6. The roll speed was 2.1 rpm and the screw speed was varied to maintain the press force. This test produced 49.3 pounds of three-dimensional shapes with 2.59 pounds of fines for a product yield of 95.0%. The capacity was 106.7 pounds per hour. The three-dimensional shapes were packaged in a similar manner to those from Test 5.

The results of Tests 1-6 are summarized in Table 1. Collectively, the CS-25 was able to produce almond-shaped three-dimensional shapes of choline chloride using a range of press forces: 30 to 115 kN. The higher the press force, the longer it took to dissolve a briquette in water. Extended runs were conducted at 60 and 100 kN with capacities of 97 and 107 pounds per hour, respectively. The CS-25 was able to produce three-dimensional shapes. Some of the material around the three-dimensional shapes that connect one briquette to the next was removed when the three-dimensional shapes slid down the 10 mm screen. An additional method for removing the material is to use a screening deck with a large opening screen. The bouncing action of the three-dimensional shapes on the screen can be used to break off the connecting material, which would then be small enough to pass through the screen.

TABLE 1

| Test Number | 1A | 1B | 2 | 3 | 4 | 5 | | 6 | |
|---|---|---|---|---|---|---|---|---|---|
| Machine Type | CS-25 | | CS-25 | CS-25 | CS-25 | CS-25 | | CS-25 | |
| Material | Choline Chloride | | Choline Chloride | Choline Chloride | Choline Chloride | Choline Chloride | | Choline Chloride | |
| Roller Type | Almond 2 Rows 30 × 20 × 14 mm | | Almond 2 Rows 30 × 20 × 14 mm | Almond 2 Rows 30 × 20 × 14 mm | Almond 2 Rows 30 × 20 × 14 mm | Almond 2 Rows 30 × 20 × 14 mm | | Almond 2 Rows 30 × 20 × 14 mm | |
| Working Width (cm) | 6.4 | | 6.4 | 6.4 | 6.4 | 6.4 | | 6.4 | |
| Hydraulic Pressure (bar) | 80 | | 80 | 80 | 80 | 80 | | 80 | |
| Accumulator Pressure (bar) | 60 | | 60 | 60 | 60 | 60 | | 60 | |
| Press Force (kN) | 60-61 | 51.5 | 31.6-32.0 | 95-100 | 115.2-116.7 | 60 | 63.8 | 99.7-99.9 | 103.7-104.4 |
| Rotor Speed (rpm) | 2.1 | 2.1 | 3.0 | 2.1 | 2.1 | 2.1 | | 2.1 | |
| Rotor Amps (Idle) | 2.4 | 2.6 | N/A | N/A | N/A | N/A | | NA | |
| Rotor Amps-Master (Load) | N/A | 3.6 | 3.3 | 5.6 | 6.8-7.0 | 3.5 | 3.9-4.1 | 5.4 | 5.3 |
| Rotor Amps-Slave (Load) | N/A | 3.9 | 3.4 | 6.8 | 7.5-7.8 | 4.8 | 3.9-4.0 | 5.3 | 5.2 |
| Screw Type | Cylindrical | | Cylindrical | Cylindrical | Cylindrical | Cylindrical | | Cylindrical | |
| Screw Speed (rpm) | 15 | 15 | 15 → 20 → 18.5 | 18.5 → 21.0 | 21.0 → 23.0 | 15.0 → 18.0 | 16.8 | 21.0 → 21.5 | 28.0 |
| Screw Amps (Idle) | N/A | N/A | N/A | N/A | N/A | N/A | N/A | N/A | N/A |
| Screw Amps (Load) | N/A | 3.5 | 3.4 | 4.9-52 | 5.2-5.6 | 3.8-3.9 | 3.4-3.7 | 3.8 | 3.5 |
| Feed Amount (lbs) | N/A | N/A | N/A | N/A | N/A | N/A | | N/A | |
| Time (min) | 3.7 | 1.0 | 1.1 | 2.0 | 2.0 | 47.9 | | 27.7 | |
| Product Amount (lbs) | N/A | N/A | N/A | N/A | 4.13 | 77.3 | | 49.3 | |
| Capacity (lbs/hr) | N/A | N/A | N/A | N/A | 123.9 | 96.8 | | 106.7 | |
| Fines Amount (lbs) | N/A | N/A | N/A | N/A | 0.19 | 5.17 | | 2.59 | |
| Dissolution Time (min) | 4.0 | N/A | 2.5 | 6.5 | N/A | N/A | | N/A | |

Example 2

Pillow-shaped three-dimensional shapes of choline chloride were formed to determine if briquetting the material reduces the surface area sufficiently to minimize or eliminate caking of the product and limit the materials ability to absorb moisture as well as identify briquette sizes and shapes that would result in ideal performance at the edges of the three-dimensional shapes.

Figure 2A:
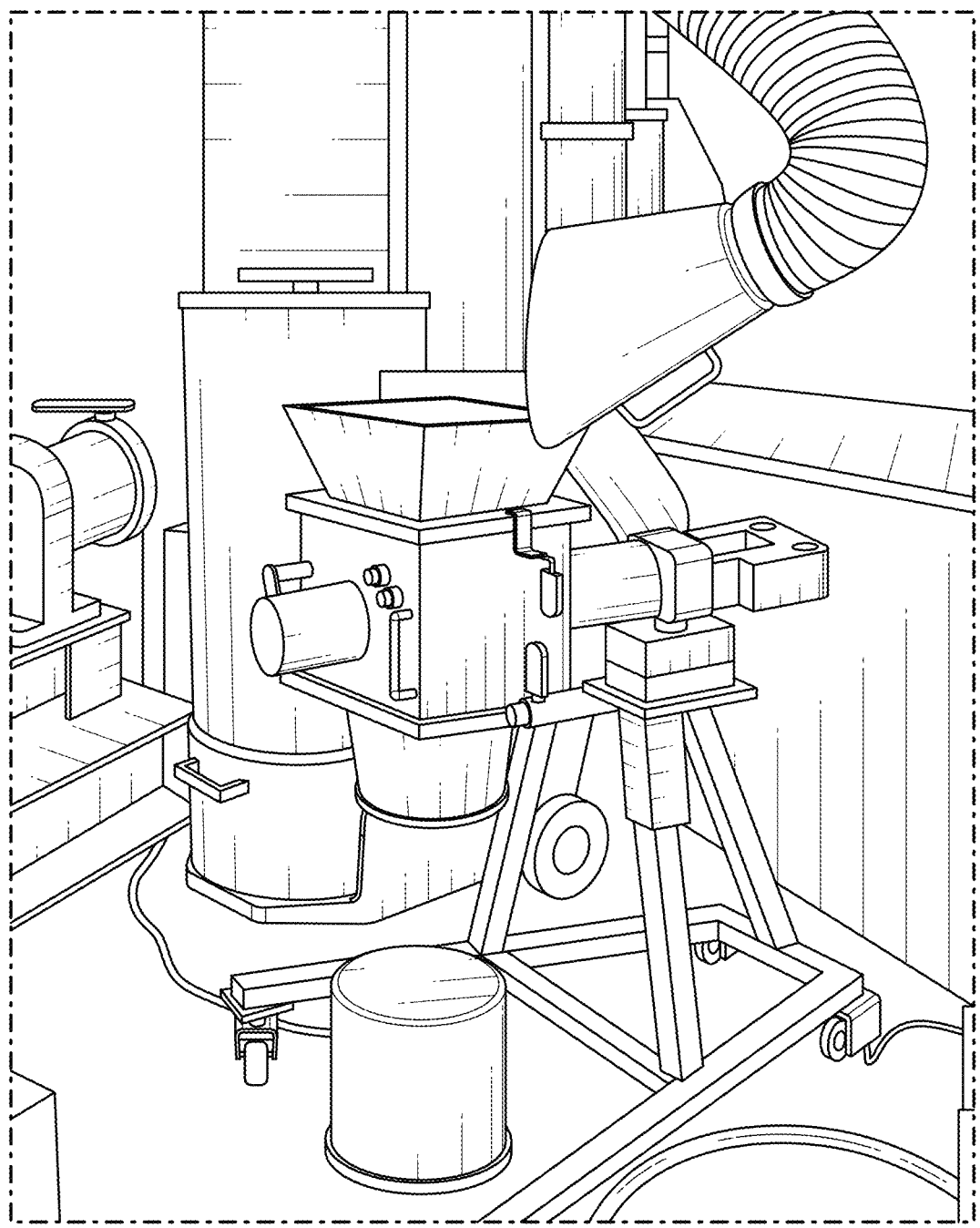
FIG. 2A is an image depicting manual feeding of choline chloride into through a Flake Crusher AFC 200.
Figure 2B:
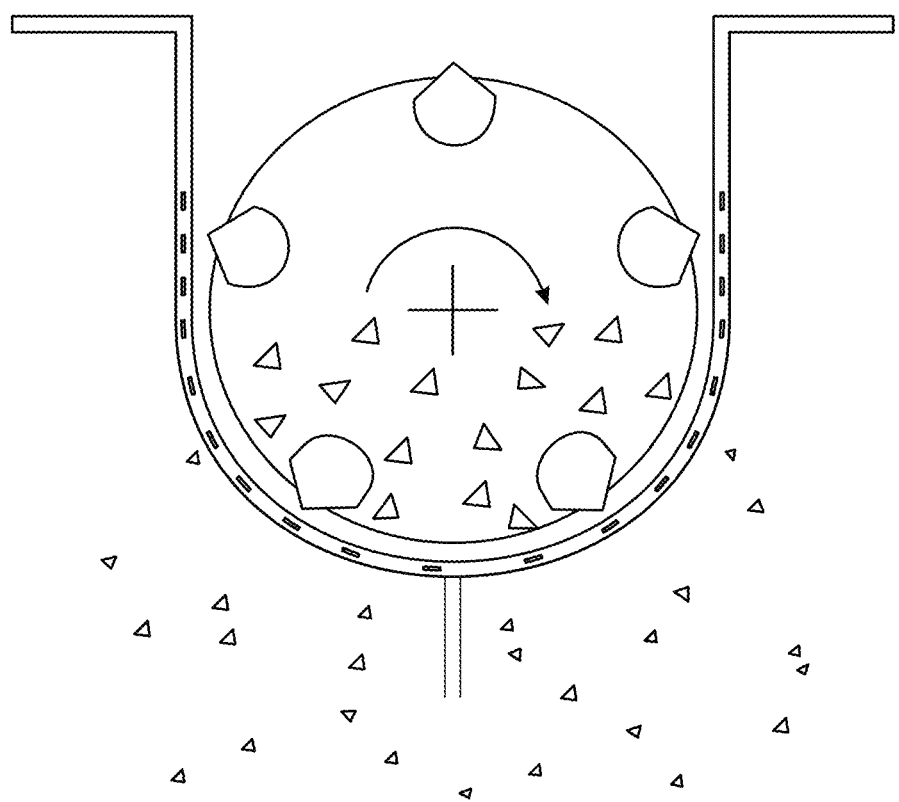
FIG. 2B is an image depicting the action of crushing choline chloride material inside a Flake Crusher AFC 200 between a rotor and a screen.
Figure 3:
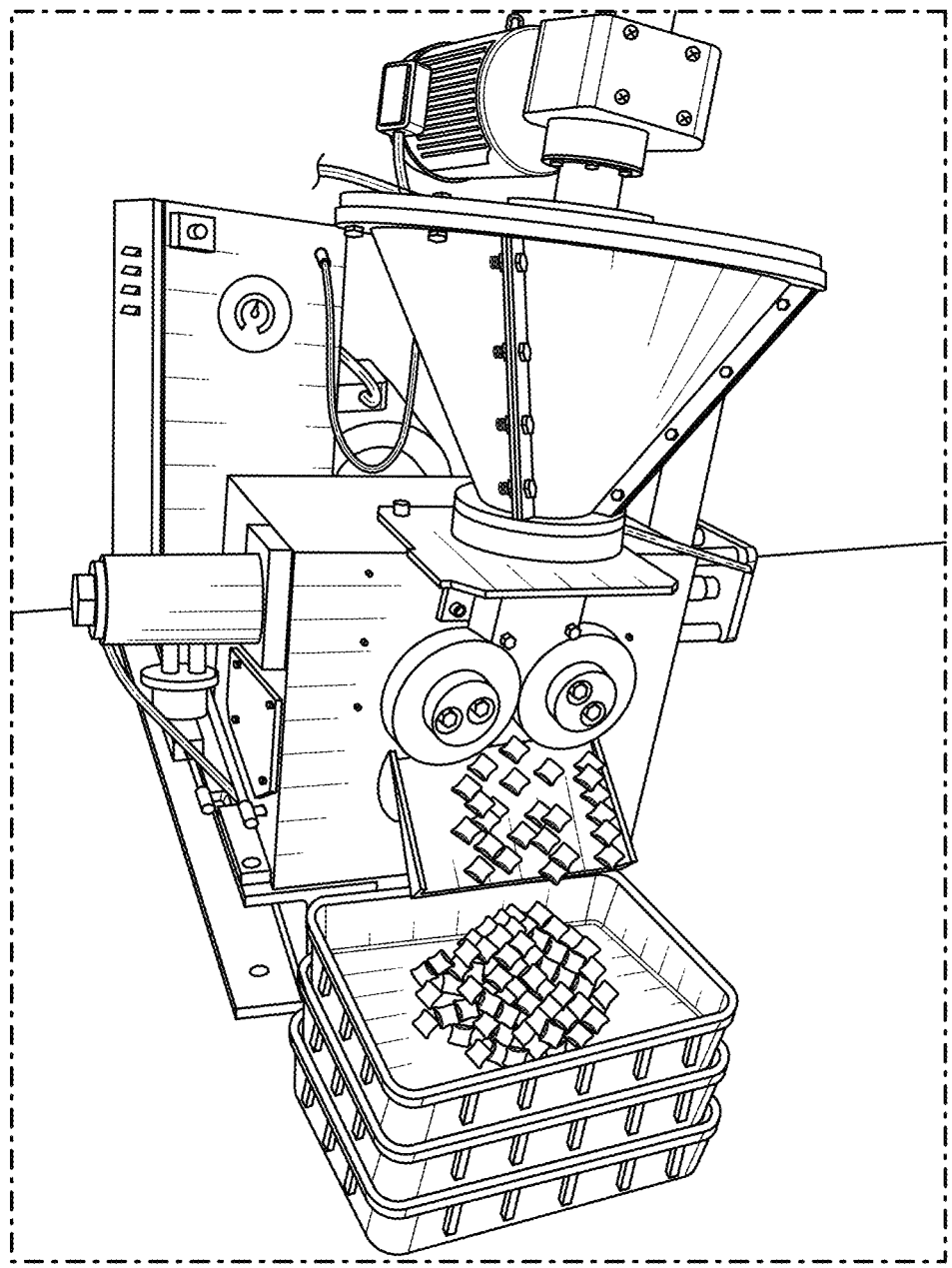
FIG. 3 is an image depicting manual feeding of choline chloride material into the feed hopper of a Hosokawa Alpine Kompaktor ARC Model CS-25 system. Also depicted in the image is a precompression screw which is rotated to feed the product into the region between two counter rotating rollers inside the Hosokawa Alpine Kompaktor ARC Model CS-25 system.

Choline chloride is highly hygroscopic. Prior to forming the three-dimensional shapes, choline chloride formed solid lumps inside the drums. This required deagglomeration of the choline chloride. Accordingly, choline chloride was fed through a Flake Crusher AFC 200 (FIG. 2A). With this machine, choline chloride material was crushed between a rotor and a screen as shown in FIG. 2B. The deagglomerated choline chloride was immediately compacted into pillow-shaped three-dimensional shapes using a Hosokawa Alpine Kompaktor ARC Model CS-25 system (hereinafter "the CS-25"). The CS-25 was equipped with briquette rollers to create the final products, 14 mm×14 mm, 24 mm×24 mm, or 30 mm×30 mm pillow-shaped three-dimensional shapes. The deagglomerated choline chloride particles were added to the feed hopper of the compactor manually and a pre-compression screw rotated to feed the product into the region between two counter rotating rollers (FIG. 3). The counter rotating rollers catch the material moving it closer to the roller surface. Both rolls were pressed to each other by means of a hydraulic system. A mechanical stopper prevented direct roller contact. As hydraulic oil is incompressible, a bladder filled with nitrogen allowed the necessary movement of the moveable roller. As the material gets closer to the roller surface, the product become more densified until a solid briquette was formed and ejected out of the bottom into a collection area. The three-dimensional shapes were then added to a shaker/screener to make the three-dimensional shapes a more uniform shape by removing edges and fines from the product. It is important to remove these fines and other loose particles because if packaged with the briquetted product, they could cause the product to bridge together and form a solid mass again.

Figure 4A:
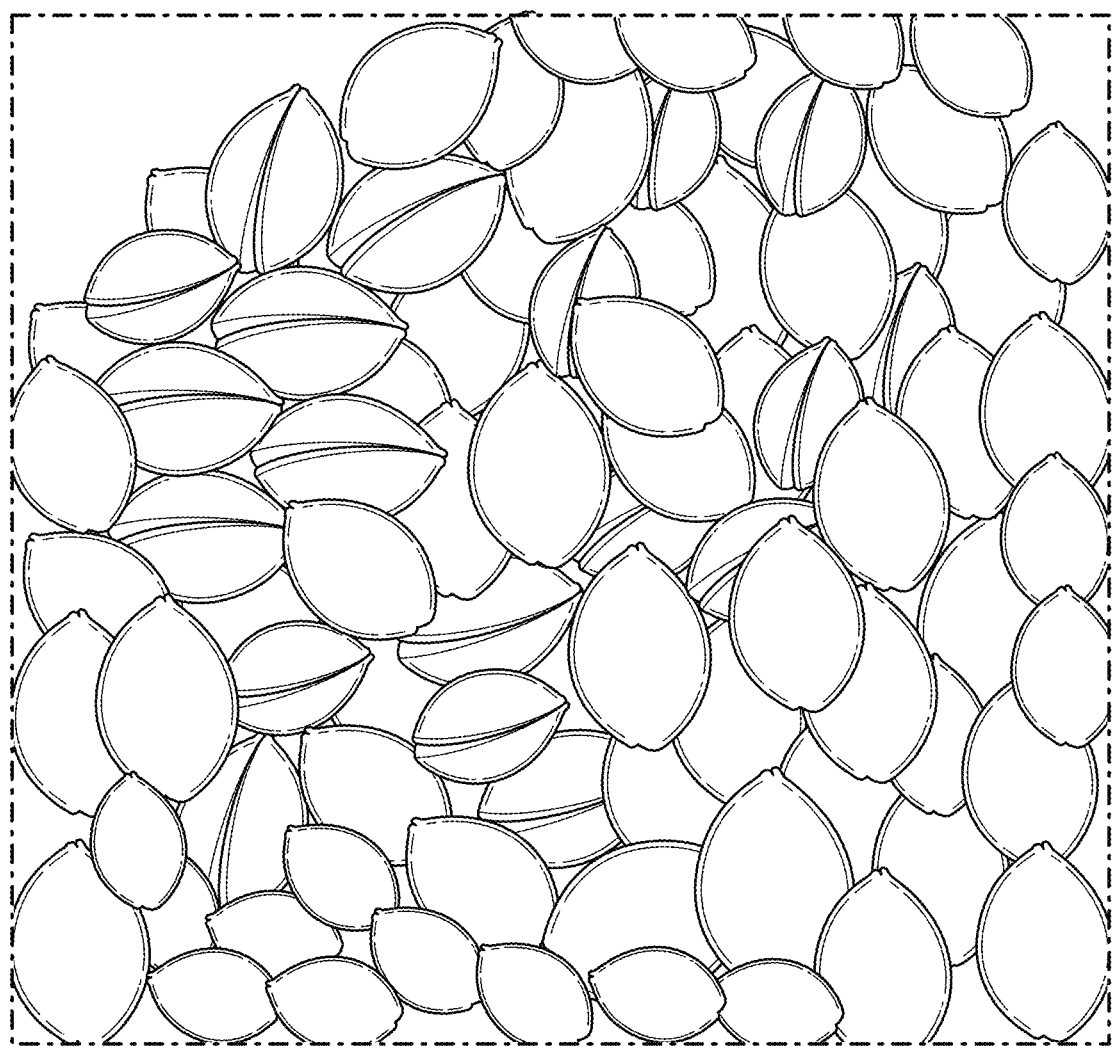
FIG. 4A is an image depicting 30 mm×30 mm pillow-shaped three-dimensional shapes of choline chloride.
Figure 4B:
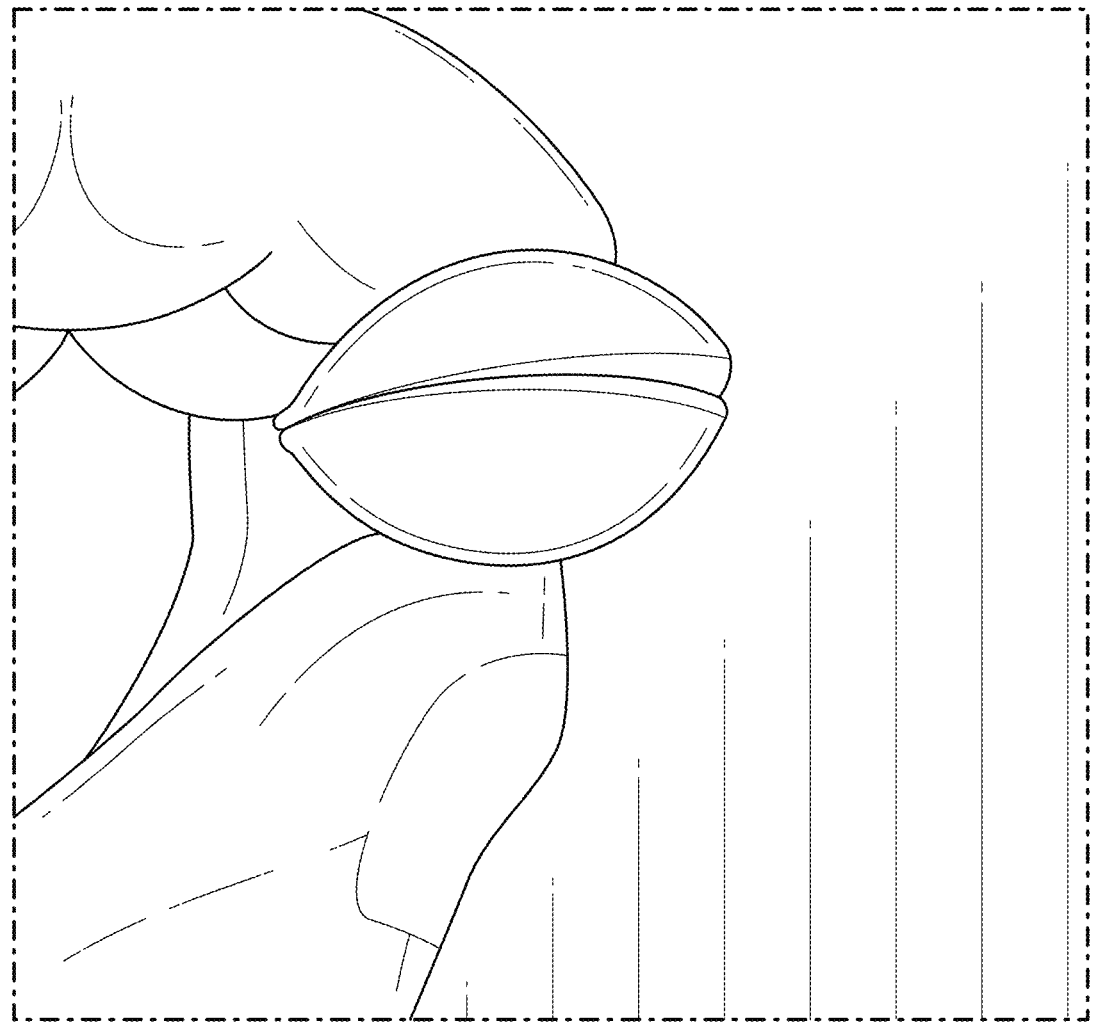
FIG. 4B is an image depicting a split in the middle of a 30 mm×30 mm pillow-shaped briquette of choline chloride.

A total of five tests were conducted to produce pillow-shaped three-dimensional shapes of choline chloride. In Test 1, briquette rollers were used to generate 30 mm×30 mm pillow-shaped three-dimensional shapes. A press force of around 80-90 kN was maintained for Test 1. The roll speed was 4 rpm and the screw speed was 45 rpm. This test produced soft three-dimensional shapes which split in the middle (FIGS. 4A and 4B). Accordingly, it was determined that this size of briquette was too big for this material. However, three-dimensional shapes of this size may be produced if the material is pre-compacted.

Figure 5A:
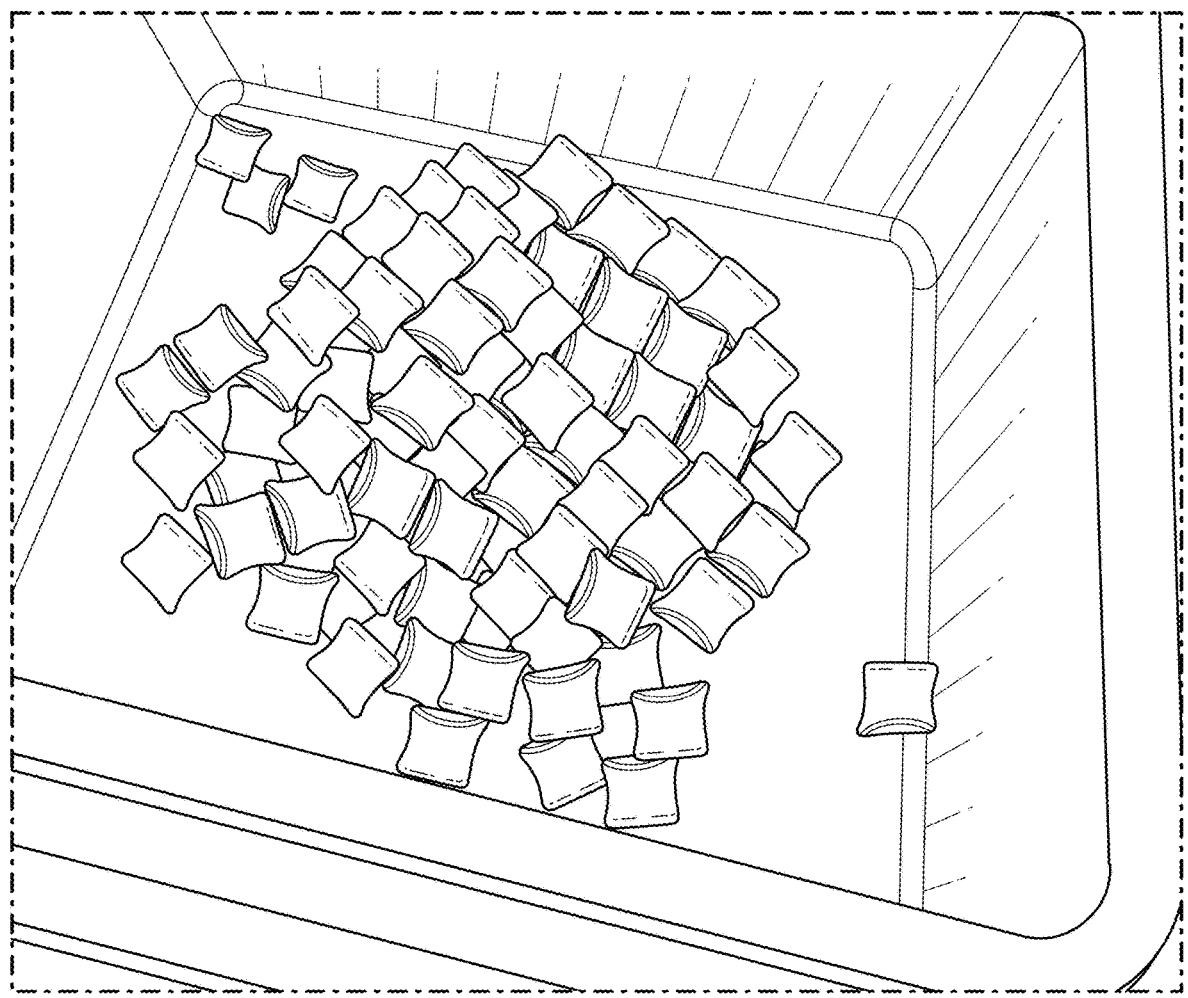
FIG. 5A is an image depicting 24 mm×24 mm pillow-shaped three-dimensional shapes of choline chloride that were generated with a press force of around 50-60 kN.
Figure 5B:
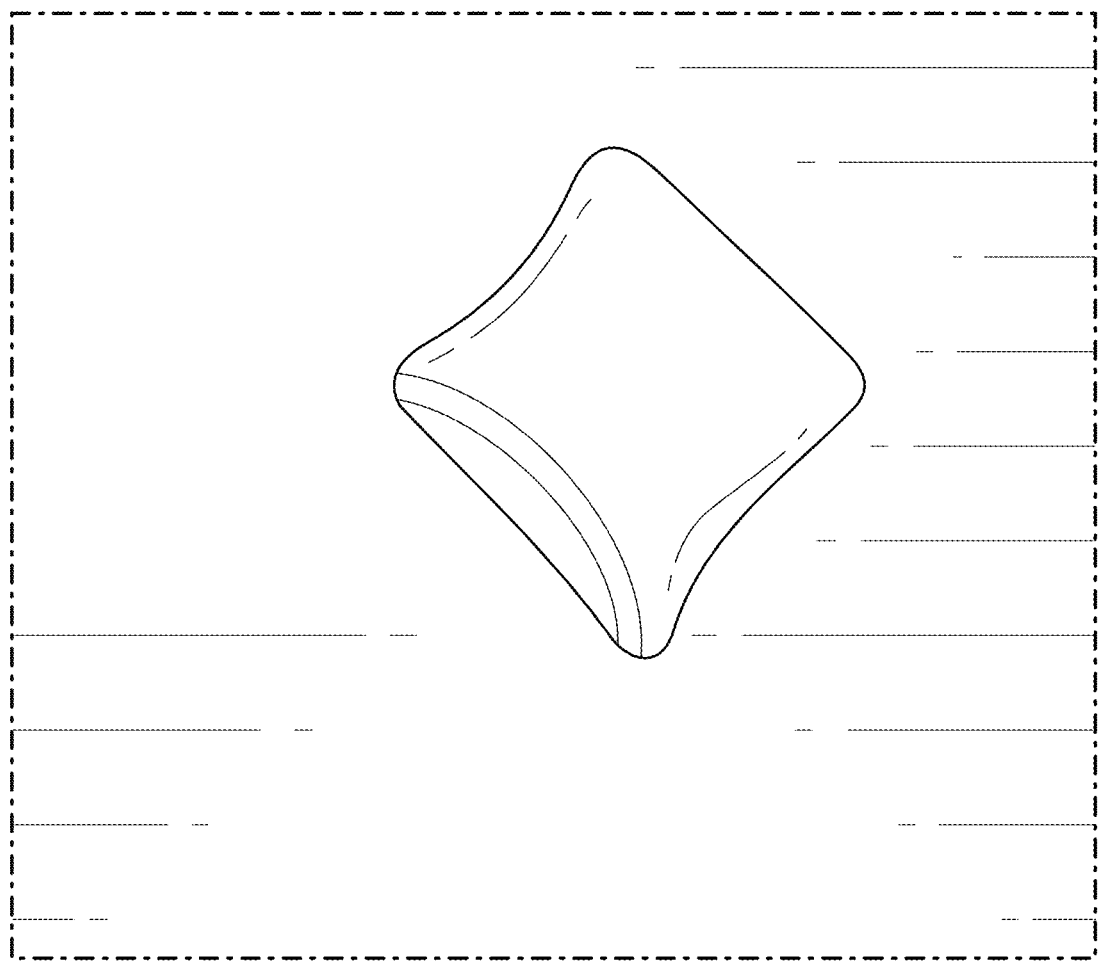
FIG. 5B is an image depicting the soft-edges of a 24 mm×24 mm pillow-shaped briquette of choline chloride that was generated with a press force of around 50-60 kN.

In Test 2, briquette rollers were used to generate 24 mm×24 mm pillow-shaped three-dimensional shapes. A press force of around 50-60 kN was maintained for Test 2. The roll speed was 4 rpm and the screw speed was 38 rpm. This process yielded a capacity gross/net of 60/57 kg/h of final product. Although this test produced nice three-dimensional shapes (FIG. 5A), the choline chloride three-dimensional shapes had soft edges (FIG. 5B).

For Test 3, briquette rollers were used to generate 24 mm×24 mm pillow-shaped three-dimensional shapes. In this test, a press force of 80 kN was maintained. The roll speed was 6 rpm and the screw speed was 99 rpm. This process yielded a gross throughput of 112 kg/h of final product. By increasing the press force to 80 kN the edges of the choline chloride three-dimensional shapes were harder than those from Test 2. The density of the choline chloride three-dimensional shapes from Test 3 was 1.28 g/cm³.

In Test 4, briquette rollers were used to generate 24 mm×24 mm pillow-shaped three-dimensional shapes. A press force of around 90 kN was maintained and the roll speed was 6 rpm. In this test, increasing the press force to 90 kN overpressed the choline chloride three-dimensional shapes and the three-dimensional shapes had cracks due to overpressing.

Figure 6A:
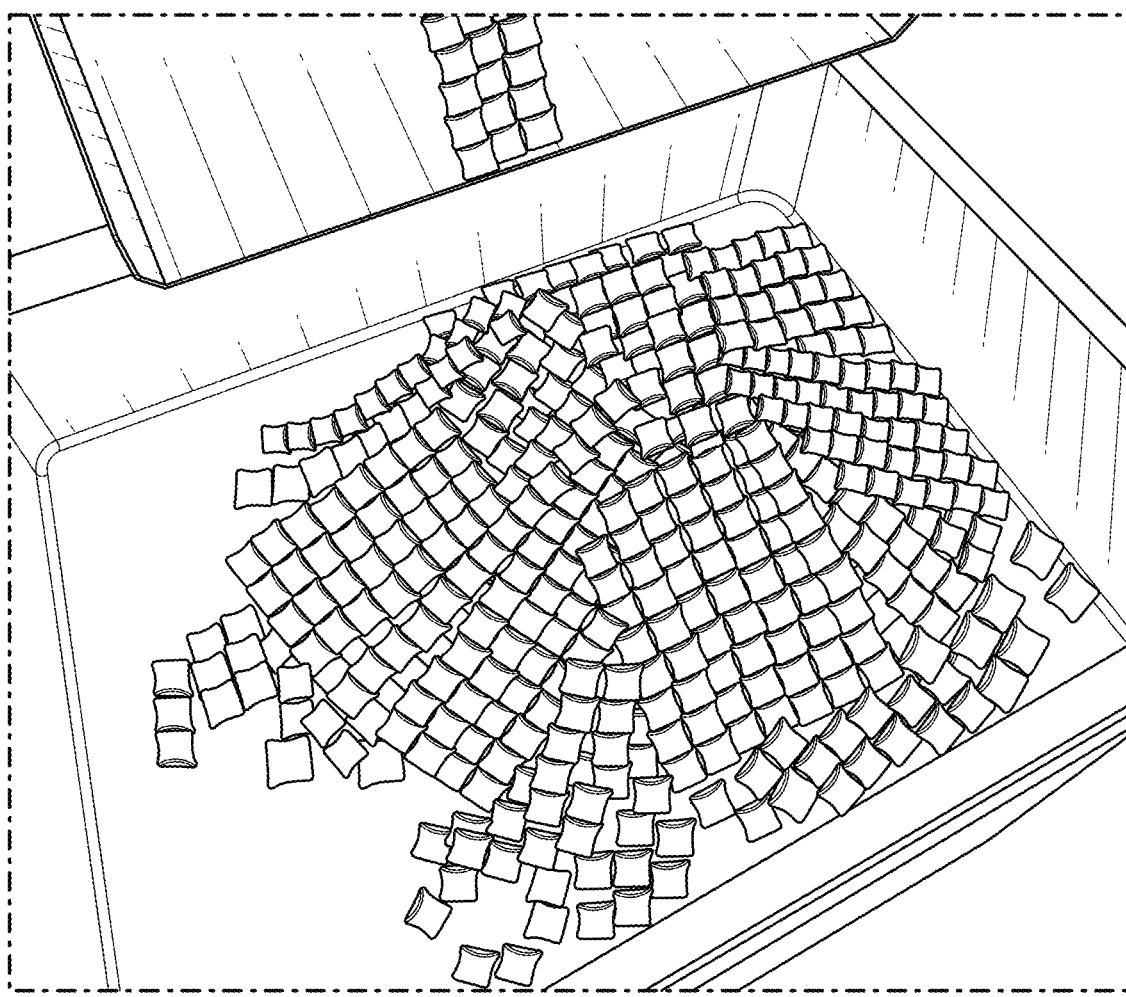
FIG. 6A is an image depicting 14 mm×14 mm pillow-shaped three-dimensional shapes of choline chloride.
Figure 6B:
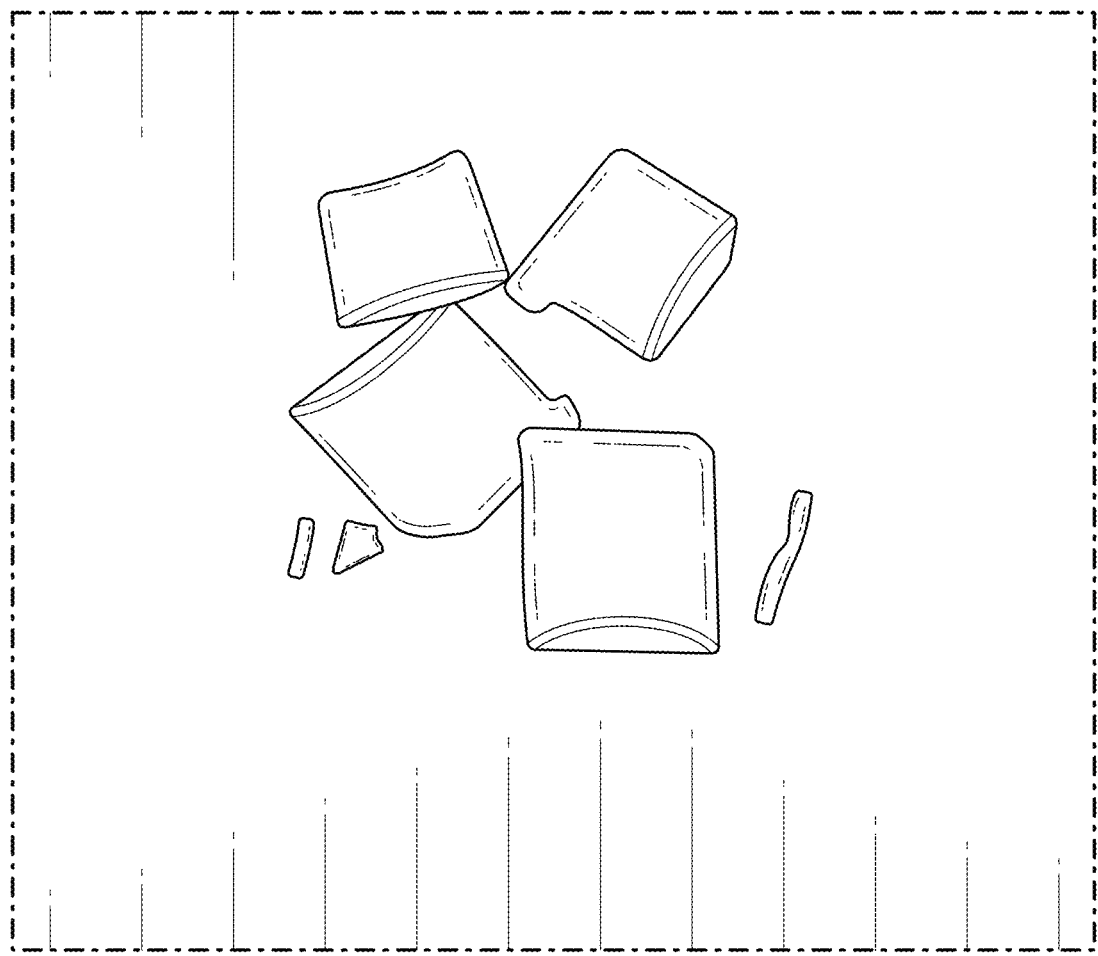
FIG. 6B is an image depicting 14 mm×14 mm pillow-shaped three-dimensional shapes of choline chloride that do not have soft-edges.

For Test 5, briquette rollers were used to generate 14 mm×14 mm pillow-shaped three-dimensional shapes. A press force of 80 was maintained for Test 5. The roll speed was 12 rpm and the screw speed was 100 rpm. This test produced nice three-dimensional shapes (FIGS. 6A and 6B) with a gross throughput of 132 kg/h final product.

The results of Tests 1-5 are summarized in Table 2. Overall, the tests demonstrated that briquetting of the choline chloride was possible. Prior to briquetting the choline chloride material had to be deagglomerated because of the material's hydroscopic behavior. The 30 mm×30 mm pillow-shaped briquette could not be briquetted into stable three-dimensional shapes. The smaller pillow shaped three-dimensional shapes 24 mm×24 mm and 14 mm×14 mm had good strength and hardness at 80 kN. Both of the smaller pillow briquette shapes had an excellent quality.

TABLE 2

| | Test Number | | | | |
|---|---|---|---|---|---|
| | 1 | 2 | 3 | 4 | 5 |
| Material | Choline Chloride | Choline Chloride | Choline Chloride | Choline Chloride | Choline Chloride |
| Bulk density dry feed material (g/l) | 446 | 446 | 446 | 446 | 446 |
| Machine type | CS-25 | CS-25 | CS-25 | CS-25 | CS-25 |
| Roller Surface | 30 mm × 30 mm | 24 mm × 24 mm | 24 mm × 24 mm | 24 mm × 24 mm | 14 mm × 14 mm |
| Working width (cm) | 6.4 | 6.4 | 6.4 | 6.4 | 6.4 |
| Hydraulic pressure (bar) | 60 | 60 | 60 | 60 | 60 |
| Accumulator pressure (bar) | 40 | 40 | 40 | 40 | 40 |
| Press force (kN) | 80-90 | 50-60 | 80 | 90 | 80 |
| Roller speed (rpm) | 4 | 4 | 6 | 6 | 12 |
| Roller drive ampere | | 8.2 | 9.1 | 9.1 | 9.1 |
| dosing | screw | screw | screw | screw | screw |
| Screw type | cylindrical | cylindrical | cylindrical | cylindrical | cylindrical |
| Screw speed (rpm) | 45 | 38 | 99 | N/A | 100 |
| Screw drive | N/A | 3.2 | 3 | N/A | 3 |
| Gross throughput (kg/h) | N/A | 60 | 112 | N/A | 132 |
| Net throughput (kg/h) | N/A | 57 | 104 | N/A | 115 |
| Yield (%) | N/A | 95% | 93% | N/A | 87% |

Example 3

Puck, briquette, and compaction tests were performed on two batches of choline chloride and one batch of choline bitartrate. Specifically, one batch of choline chloride (old batch) was kept exposed to ambient temperature and humidity for 5 days prior to testing. During that time, the choline chloride (old batch) sample liquefied and hardened into a solid mass. The second batch of choline chloride (new batch) remained sealed until testing, preventing the material from prior exposure to ambient temperature and humidity.

Figure 7A:
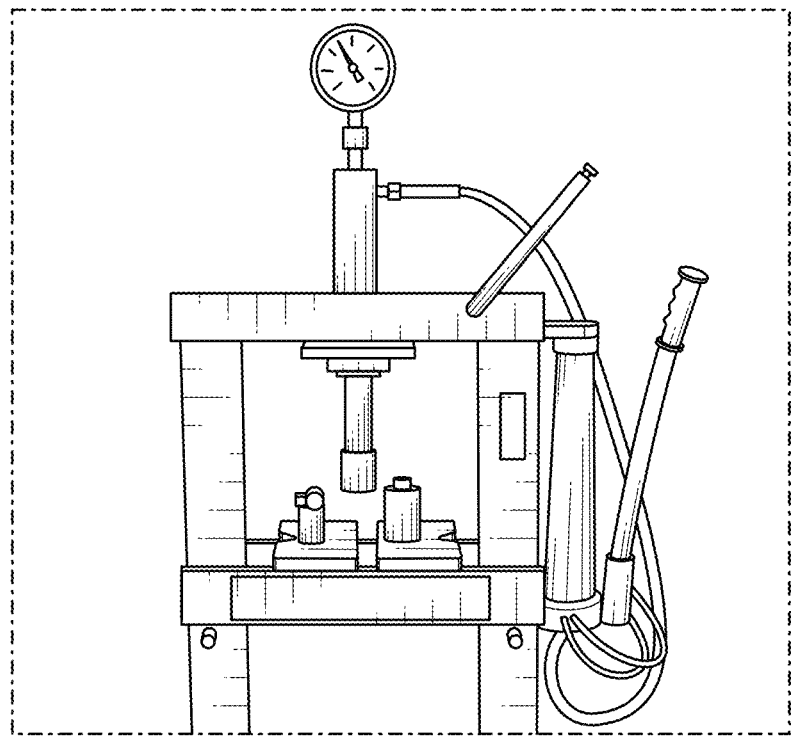
FIG. 7A is an image depicting the manual press used to conduct puck and briquette tests.
Figure 7B:
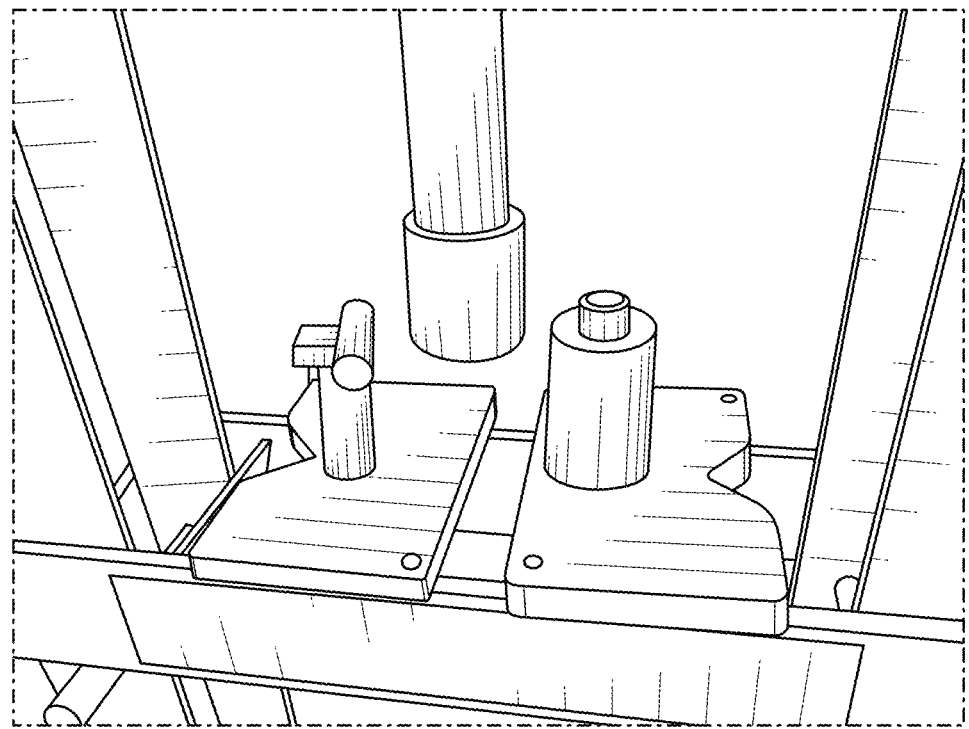
FIG. 7B is an image depicting the die sets used to conduct puck and briquette tests.

The first test of the three materials was a puck test. This test determined the tonnage required to effectively compact the choline chloride and choline bitartrate batches by measuring the compaction load required by tons/inch. Using a one inch standard die allowed for a direct translation of the load required between a manual press and a Ludman 1604 Briquetter. The die was made from stainless steel, and was thoroughly washed down before use. The second test, a briquette test, utilized a custom die machined to produce three-dimensional shapes that simulate the shape, size and properties of the three-dimensional shapes produced in large-scale using a Ludman 1604 Briquetter. This die was also made of stainless steel. The test apparatus and die sets for puck and briquette tests are shown in FIGS. 7A and 7B. The puck and briquette tests were designed to verify minimum compaction force and verify free release of the material from the dies.

The choline chloride (new batch) was generally free flowing material that had developed only slight clumping in transit. Three standard pucks were produced from the new batch of the choline chloride. Loads of 8, 9, and 10 tons, respectively, were applied to the pucks for this test. At all loads, the outer surface of the pucks was fully compacted with no granular appearance on the outer surface. Increasing the load from 8 to 10 tons also did little to change the density of the puck. Each puck produced was approximately 15/16" wide, and all 3 pucks weighed between 12.3 and 12.6 grams. Three three-dimensional shapes were also produced with the new batch of choline chloride. The load range was lowered to 7, 8, and 9 tons for this sequence of tests to see the variance of material response. At the 7 ton load, the briquette had a fully compacted outer surface, but was quite easy to break apart, and much of the center of the briquette was visibly granular. Under the 8 ton load, the briquette was still breakable, and had a visual center sliver of granular material. Under the 9 ton load, the briquette produced was not breakable by hand, indicating thorough compaction.

The old batch of choline chloride showed rapid hardening of the material when stored for even a short time. In order to collect enough material for the puck tests, the hardened material was chiseled before compaction. Overall, the choline chloride (old batch) of material required higher loads than the choline chloride (new batch) to fully compact. The puck test required 11 tons to fully compact the choline chloride (old batch), rather than 10 tons for the choline chloride (new batch). The briquette tests supported the puck tests. While the choline chloride (new batch) only needed a 9 ton load to fully compact, the choline chloride (old batch) required a 10 ton load.

The choline bitartrate batch was more free-flowing than either the old or new batches of choline chloride. By appearance, there was a noticeable difference between the two types of material. The chloride materials had a more granular appearance, while the bitartrate had a less uniform appearance where each particulate had a somewhat crystallized appearance. Though the choline bitartrate was more free-flowing than either batch of choline chloride, it also was more difficult to compact. For both the puck tests and the briquette tests, under the same loads as the choline chloride batches, the choline bitartrate failed to agglomerate. Three-dimensional shapes were made under the same loads, but they were easily damaged or broken. Light rubbing of the outer surface of the pucks caused the pucks to wear, and light pressure to the edges of the pucks caused deformation. Significantly higher loads, ranging above those provided by large-scale Ludman briquetters, would be required to properly agglomerate the choline bitartrate.

Figure 8:
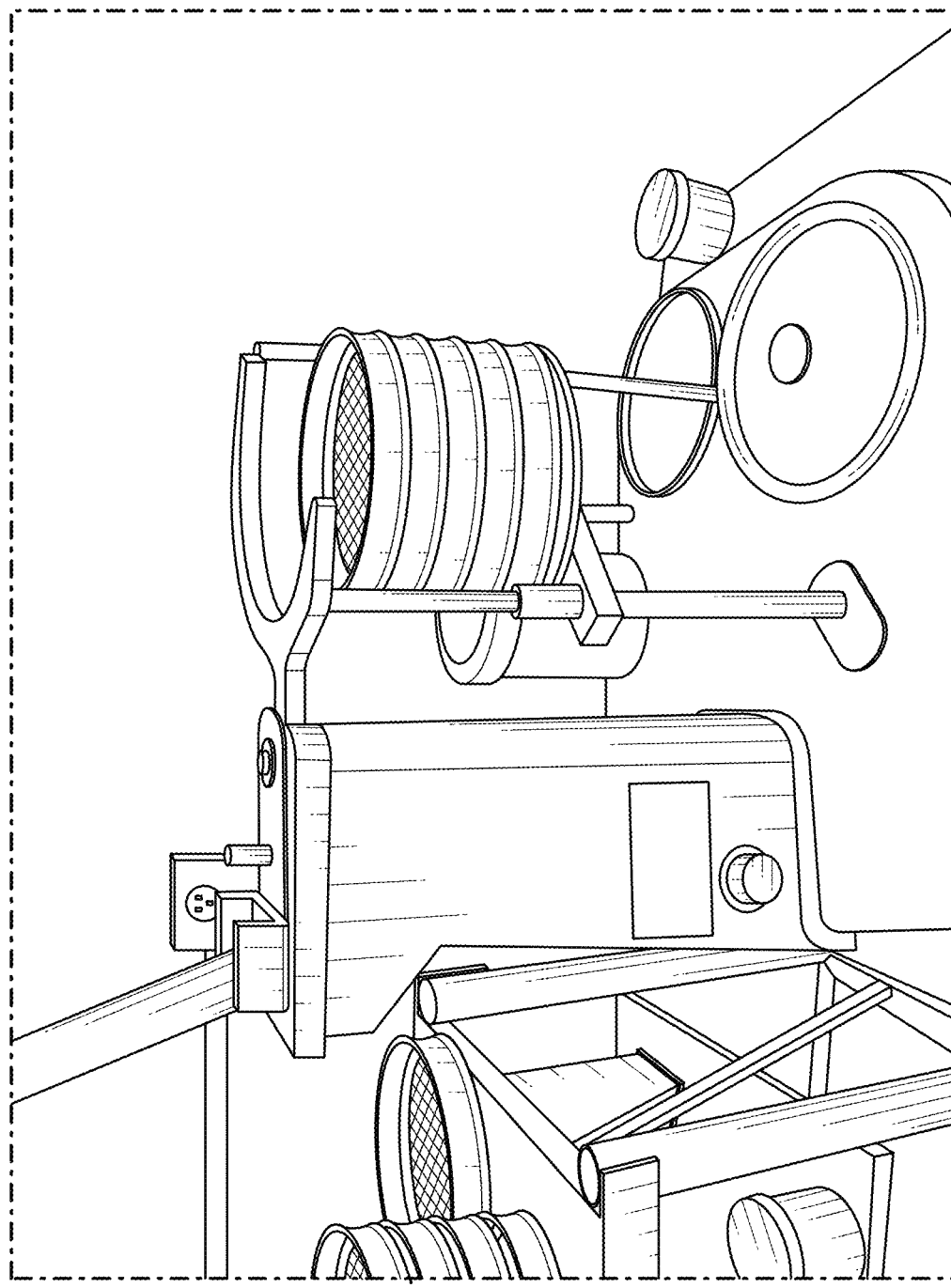
FIG. 8 is an image depicting a Rotap sieve shaker fitted with a 5/16" sieve screen and multiple, finer screen sizes underneath the 5/16" sieve screen.

Three-dimensional shapes from the choline chloride old and new batch tests were saved, intact, to perform a follow-up Rotap test. The Rotap test was arranged to simulate the screening of material after compaction and determine briquette strength. Three-dimensional shapes were placed on a ⅝16" sieve screen with multiple finer screen sizes underneath (FIG. 8). An approximate 90 second simulation was run on the Rotap sieve shaker. After being shaken on the screen for 90 seconds with the Rotap hammer providing vertical impact on the screen, 100% of the three-dimensional shapes from both the old and new choline chloride batches remained intact.

Figure 9A:
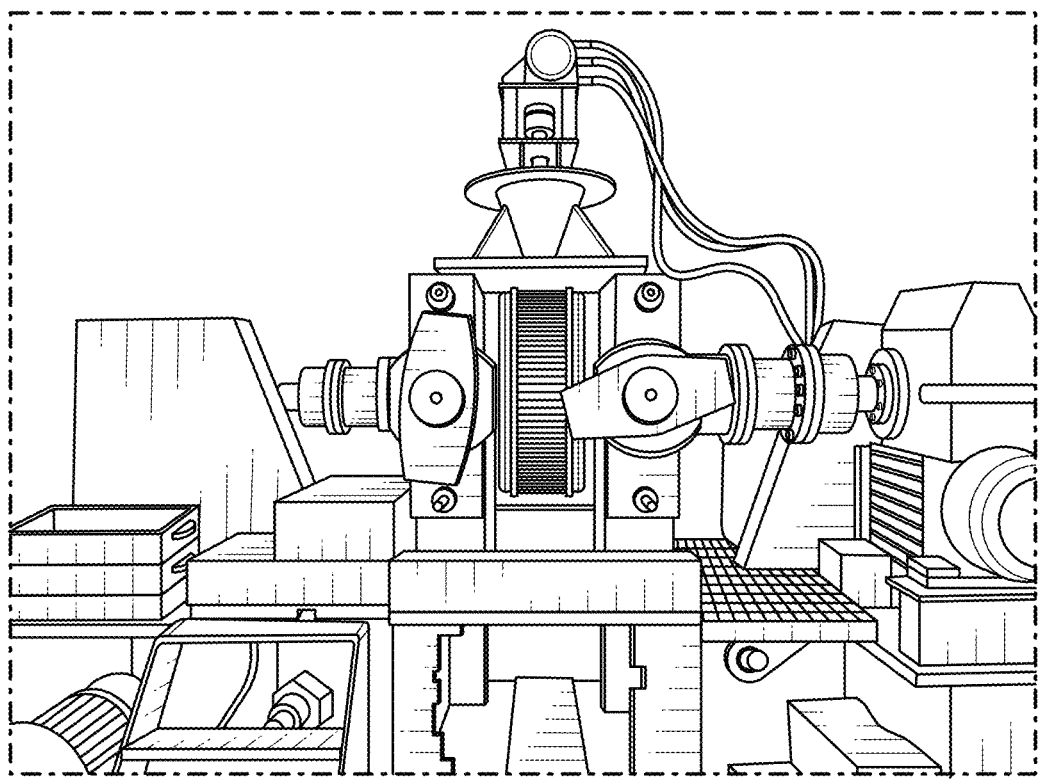
FIG. 9A is an image depicting the Ludman 3005 lab compactor used to conduct large-scale compaction tests.
Figure 9B:
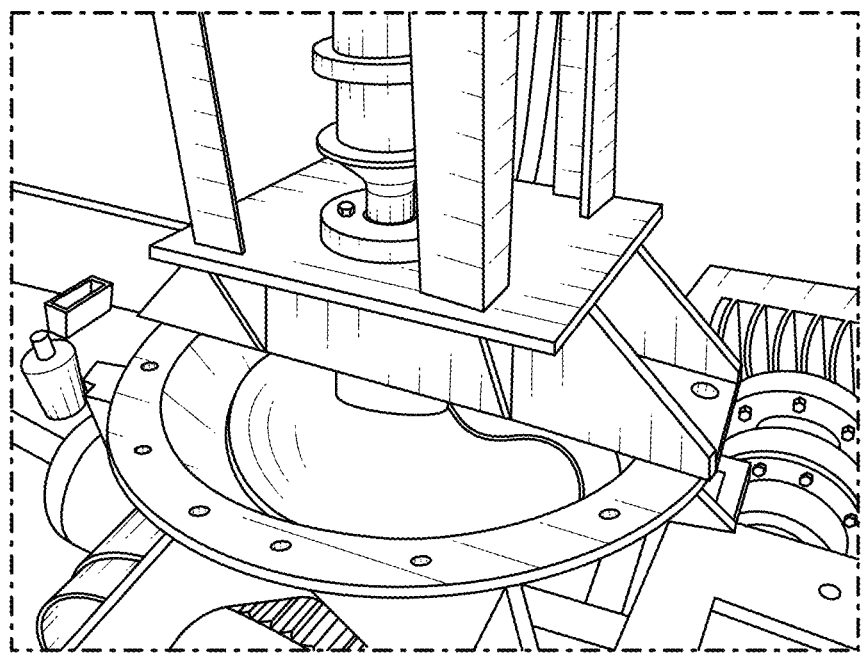
FIG. 9B is an image depicting a Ludman 3005 lab compactor fitted with a narrow roll face and a force feeder to pre-densify the material before reaching the compaction nip zone.

A large-scale compaction test was performed on the old and new choline chloride batches using the Ludman 3005 lab compactor (FIG. 9A). Similar to the 1604 Ludman briquetter, the lab compactor had a narrow roll face, and a force feeder to pre-densify the material before reaching the compaction nip zone (FIG. 9B). Every 100 psi applied to the Ludman 3005 lab rolls is equivalent to 1 ton/inch load added to the roll face.

To mirror the loads of the puck test with the new batch of choline chloride, a 1000 psi (10 tons/inch) pressure was applied to the cylinders. The roll gap used for the initial compaction tests was 0.090 inches. The choline chloride new batch material was unaltered upon removing it from the sealed container. Early tests showed unified compaction of the choline chloride new batch material across the entire roll face. The material did not cause the rolls to retract, and the product created matched the roll gap at 0.090 inches thick. The thin nature of the choline chloride (new batch) material and the relatively low roll pressure caused early tests at 1000 psi and 1350 psi to be relatively weak and easily broken. Raising the roll pressure to 1600 psi (16 tons/inch) resulted in sufficient compaction force to make hard flake completely across the roll face. At this point, a test was run to see the effect of increasing the roll gap from 0.090 inches to 0.210 inches. Instead of making a hard consistent material, the new batch of choline chloride failed to compact at all. The roll gap was narrowed back to 0.090 inches for all remaining tests.

As the material supplied in the old batch of the choline chloride had liquefied and hardened into a solid mass, the material was chiseled into smaller chunks before sending it through the force feeder. These chunks caused the force feeder to stall. For large-scale production of three-dimensional shapes made of the old batch of choline chloride, a high torque motor is required on the force feeder in order to properly flow the old batch of the choline chloride into the 1604 Ludman Briquetter. For the testing purposes herein, the chunks of material were sent through Ludman 6-inch lab granulators to break up the chunks of choline chloride (old batch) material before compaction. When this was done, the force feeder no longer stalled for any of the subsequent steps.

Knowing the new batch of choline chloride compacted sufficiently at 1600 psi, and the old batch of choline chloride needed a higher pressure than the new batch of choline chloride to create pucks, the first compaction test for the old batch of choline chloride was performed at 1600 psi. As expected, the flake was soft at this pressure. Subsequent tests were performed until the conclusion was made that 2000 psi (20 tons/inch) was a sufficient pressure to compact the old batch of the choline chloride.

The results of the tests are summarized in Table 3. The puck, briquette, and compaction tests demonstrated that choline chloride can be sufficiently briquetted using the large-scale Ludman 1604 Briquetter. Choline chloride three-dimensional shapes will hold shape if screened immediately after agglomeration. No wear was shown as a result of the screening process. Choline chloride flows to fill gaps extremely well during compaction using a force feeder. A 25 or 30 horsepower (hp) motor will be required on the force feeder to sufficiently pre-densify the material in the nip zone. Choline chloride tends to clump if sitting for any extended period of time, and those clumps will need sufficient horsepower to translate through the tighter screw pitches in the force feeder. The results showed that the tighter the gap between the rolls, the better the choline chloride compacts and that mixtures of choline chloride sufficiently compact between 16 tons/inch and 20 tons/inch, depending on the shelf life of the material being compacted.

Puck and briquette tests showed that although choline bitartrate does compact, the material does not sufficiently agglomerate like the choline chloride. The compacted pucks were easily worn down under pressure, and the three-dimensional shapes did not fully compact at the surface, causing them to stick in the briquette pockets and not freely release.

TABLE 3

| Test Number | Material | Product | Tonnage | Pressure | Notes |
|---|---|---|---|---|---|
| 1 | Choline Chloride (New) | Puck | 8 | | 15/16" length. 12.3 gram wt. Shiny surface across entire puck face. |
| 2 | Choline Chloride (New) | Puck | 9 | | 15/16" length. 12.3 gram wt. Increased pressure provided no negligible difference to size of puck. |
| 3 | Choline Chloride (New) | Puck | 10 | | 15/16" length. 12.6 gram wt. Still no noticeable difference in size of puck. |
| 4 | Choline Chloride (New) | Briquette | 7 | | Full briquette release. Easily breakable by hand. Surface of material solid. Center remained granular. |
| 5 | Choline Chloride (New) | Briquette | 8 | | Full briquette release. Difficult to break. Sliver of granule in center of briquette. |
| 6 | Choline Chloride (New) | Briquette | 9 | | Full briquette release. Not breakable without excess force |
| 7 | Choline Chloride (Old) | Puck | 9 | | Shiny outer surface. High pressure to edges of puck caused permanent deformation. |
| 8 | Choline Chloride (Old) | Puck | 11 | | Shiny outer surface. Maintained shape after high pressure to edges. |
| 9 | Choline Chloride (Old) | Briquette | 9 | | Solid outer shell with shine on surface. Slight granular removal with significant pressure. Could be broken, altered with significant pressure. |
| 10 | Choline Chloride (Old) | Briquette | 10 | | Solid outer shell with shine on surface. Smooth surface unaltered with pressure. |
| 11 | Rotap Test | | | | Various pucks from tests 1 thru 10 placed on 5/16" mesh screen and sent through Rotap. Three-dimensional shapes held shape with no damage with Rotap and hammer for approx 1.5 minute test. |
| 12 | Choline Bitartrate | Puck | 10 | | Using same test parameters as both Old and New Choline Chloride, Choline Bitartrate was less successful in compacting, could still see visual granular material in puck. Light contact caused |
| 13 | Choline Bitartrate | Briquette | 9 | | Same issues as above. Material also did not release from die. First case of this happening in all briquette tests. Attempt to increase pressure to see if release occurs. |
| 14 | Choline Bitartrate | Briquette | 10 | | Lower briquette die released after compaction. Material still granular. When trying to separate from top die, broke briquette apart. Significantly higher pressure required to briquette Choline Bitartrate. |
| 15 | Choline Chloride (New) | Compactor | | 1000 | Roll gap set at 0.090". 2 buckets of choline chloride sent through machine. Full flake created. Very soft. Fresh bagged material broke up by dropping bag on the ground. |
| 16 | Choline Chloride (New) | Compactor | | 1350 | Slight increase in hardness from 1000 psi. Run subsequent test to determine where sufficient hardness occurs. |
| 17 | Choline Chloride (New) | Compactor | | 1600 | Significant increased hardness. Sample supplied to Balchem. |
| 18 | Choline Chloride (New) | Compactor | | 1600 | Opened roll gap to .210" to try and draw more compacted material through. 0% of material compacted as a result of the gap increase. |
| 19 | Choline Chloride (Old) | Compactor | | 1600 | Closed roll gap back to .090". Material required impact from hammer to break to large chunks, made flowable by passing through Ludman 3LP granulator. Soft flake made at 1600 psi. |
| 20 | Choline Chloride (Old) | Compactor | | 1800 | Slight increase in hardness from 1600 psi on flake. Still did not reach hardness of "New" material at 1600 psi. |
| 21 | Choline Chloride (Old) | Compactor | | 2000 | Hardness matched that of New material at 1600 psi. Sample supplied to Balchem. |

Example 4

The 24 mm×24 mm pillow-shaped three-dimensional shapes produced in Test 3 from Example 2 were used to fill three approximately 25 kg drums for stability testing. The three-dimensional shapes were double bagged in 3 mm, 26×48, clear high density polyethylene bags; bags were closed with zip ties; and then the drum lid was secured with clear packing tape. Desiccant bags were not placed between the two liners or anywhere in the drum at any point in the testing, in order to model a worst-case scenario. The drums were stored at ambient temperatures, which ranged between 20° F. and 105° F. At various times, the contents of one drum were sampled. The bag was then re-closed with a zip tie and the drum lid re-secured.

The samples were tested as specified by the United States Pharmacopoeia 38th Revision (USP 38) monograph for choline chloride, pH, limit of total amines (measured as TMA), water determination, and chromatographic purity (6 month only). The visual appearance of the product and comments relating to its manipulability were also recorded at each time. Results from this study are provided in Table 4. The samples showed excellent handling out to 17 months, and met USP specifications out to about a year. Although the samples had more moisture than allowed by the USP specification at 15 months and 17 months, it is believed this result is attributable to the design of the study—i.e., the drum was opened multiple times, exposing the product to additional moisture. Results from formal stability studies (see, for a description see Example 5), are expected to demonstrate that the product meets specifications of the USP monograph for choline chloride after storage for greater than one year. Stability after storage for two years or more is expected.

Example 5

Three-dimensional shapes manufactured in accordance with the present disclosure are filled into 10 kg, heat-sealed foil bags and then placed into a box for stability testing (two bags per box). Desiccant packets are not used at any point in the testing. Stability is evaluated under two conditions: 25° C. and 60% relative humidity (standard stability study), and 40° C. and 75% relative humidity (accelerated stability study). At least one bag will be evaluated per time point, per condition as shown in Table 5, meaning that a bag will not be re-sealed and the contents re-evaluated at later time points. At least one sample from each bag is tested as specified by the United States Pharmacopoeia 38th Revision (USP 38) monograph for choline chloride. It is expected that the product meets specifications of the USP monograph for choline chloride after storage for greater than one year. Stability after storage for two years or more is expected.

TABLE 5

|  | 3 months | 6 months | 9 months | 12 months | 15 months | 18 months | 21 months | 24 months |
|---|---|---|---|---|---|---|---|---|
| Standard | X | X | X | X | X | X | X | X |
| Accelerated | X | X | X | | | | | |

What is claimed is:

1. A composition comprising three-dimensional shapes, wherein each shape consists essentially of choline chloride, and no dimension of each shape may measure more than 50 mm or less than 5 mm, and wherein the choline chloride has a concentration of at least 90 wt %.

2. The composition of claim 1, wherein the three-dimensional shape is selected from the group consisting of spheres, cones, disks, shields, rectangles, sticks, cubes, triangles, ovals, bullets, shells, barrels, eggs, pucks, bricks, arrowheads, compound cups, arc triangles, pillows, diamonds, half-moons, and almonds.

3. The composition of claim 1, wherein each shape has a uniform density.

4. The composition of claim 1, wherein the density of each shape is no more than about 2.0 g/cm$^3$.

TABLE 4

|  | 6 months | 10 months | 15 months | 17 months |
|---|---|---|---|---|
| Choline chloride Assay % | 99.5 | 99.3 | 99.6 | 99.4 |
| water % | 0.5 | 0.4 | 0.7 | 0.6 |
| Trimethylamine (TMA), ppm | 1 | 1 | 0.8 | 2 |
| pH | 6.2 | 6.3 | 5.3 | 6.7 |
| Chromatographic Purity | 0.02%/0.05% | | | |
| Comments | Able to scoop at the top. Need to shake or knock container by hand to separate the briquettes at the bottom of the drum. Briquettes remained intact. | Able to scoop at the top. Need to shake or knock container by hand to separate the briquettes at the bottom of the drum. Briquettes remained intact. | Able to scoop at the top. Need to shake or knock container by hand to separate the briquettes at the bottom of the drum. Briquettes remained intact. | Able to scoop at the top. Need to shake or knock container by hand to separate the briquettes at the bottom of the drum. Briquettes remained intact. |

5. The composition of claim 1, wherein the volume of each shape is no more than about 10 cm³.

6. The composition of claim 1, wherein the hardness of each shape as measured immediately after production is at least about 40 N.

7. The composition of claim 1, wherein the hardness of each shape as measured after about 6 months of storage is at least about 40 N.

8. The composition of claim 1, wherein no more than 20% fines (product not compacted into three-dimensional form) remain from the compaction process.

9. The composition of claim 1, wherein the visual dissolution time of each shape is no more than about 10 minutes using USP Apparatus II (paddles), at 100 rpm, in 900 mL of water at 37° C.

10. The composition of claim 1, wherein the composition comprises no more than 0.5% water immediately after production, as determined by Method I <921> USP 38.

11. The composition of claim 1, wherein the composition comprises no more than 0.5% water after one year of storage in moisture resistant packaging, as determined by Method I <921> USP 38.

12. The composition of claim 1, wherein the composition does not substantially cake after storage of at least one year in moisture resistant packaging.

13. A composition comprising three-dimensional shapes, wherein each shape consists essentially of choline chloride, wherein the composition is obtained by a process comprising the steps of (a) providing material consisting essentially of choline chloride and (b) compacting the material to produce a solid three-dimensional shape wherein no dimension of the shape may measure more than 50 mm or less than 5 mm, wherein the choline chloride has a concentration of at least about 90 wt %.

14. The composition of claim 13, wherein the composition does not substantially cake after storage of at least one year in moisture resistant packaging.

15. The composition of claim 13, wherein the three-dimensional shape is selected from the group consisting of spheres, cones, disks, shields, rectangles, sticks, cubes, triangles, ovals, bullets, shells, barrels, eggs, pucks, bricks, arrowheads, compound cups, arc triangles, pillows, diamonds, half-moons, and almonds.

16. The composition of claim 13, wherein the density of each shape is uniform.

17. The composition of claim 13, wherein the density of each shape is no more than about 2.0 g/cm³.

18. The composition of claim 13, wherein the volume of each shape is no more than about 10 cm³.

19. The composition of claim 13, wherein the hardness of each shape as measured immediately after production is at least about 40 N.

* * * * *